US010759878B2

(12) United States Patent
Bobula et al.

(10) Patent No.: US 10,759,878 B2
(45) Date of Patent: Sep. 1, 2020

(54) METHOD OF CROSSLINKING OF POLYSACCHARIDES USING PHOTOREMOVABLE PROTECTING GROUPS

(71) Applicant: Contipro a.s., Dolni Dobrouc (CZ)

(72) Inventors: Tomas Bobula, Svit (SK); Radovan Buffa, Humenne (SK); Pavlina Prochazkova, Vikos (CZ); Vladimir Velebny, Zamberk (CZ)

(73) Assignee: Contipro a.s., Dolni Dobrouc (CZ)

( * ) Notice: Subject to any disclaimer, the term of this patent is extended or adjusted under 35 U.S.C. 154(b) by 190 days.

(21) Appl. No.: 15/736,113

(22) PCT Filed: Jun. 14, 2016

(86) PCT No.: PCT/CZ2016/000065
§ 371 (c)(1),
(2) Date: Dec. 13, 2017

(87) PCT Pub. No.: WO2016/202314
PCT Pub. Date: Dec. 22, 2016

(65) Prior Publication Data
US 2018/0179302 A1 Jun. 28, 2018

(30) Foreign Application Priority Data
Jun. 15, 2015 (CZ) ............... PV 2015-398

(51) Int. Cl.
| C08B 37/00 | (2006.01) |
| C08B 37/08 | (2006.01) |
| C08B 15/00 | (2006.01) |
| A61K 47/61 | (2017.01) |
| A61K 47/36 | (2006.01) |
| A61K 47/38 | (2006.01) |
| A61L 27/20 | (2006.01) |
| A61L 31/04 | (2006.01) |
| C08B 11/12 | (2006.01) |

(52) U.S. Cl.
CPC .......... *C08B 37/0072* (2013.01); *A61K 47/36* (2013.01); *A61K 47/38* (2013.01); *A61K 47/61* (2017.08); *A61L 27/20* (2013.01); *A61L 31/042* (2013.01); *C08B 11/12* (2013.01); *C08B 15/005* (2013.01); *C08B 37/0069* (2013.01)

(58) Field of Classification Search
CPC . C08B 37/0072; C08B 11/12; C08B 37/0069; A61L 27/20; A61K 47/38
See application file for complete search history.

(56) References Cited

U.S. PATENT DOCUMENTS

| 3,075,527 A | 1/1963 | Bechtold |
| 3,720,662 A | 3/1973 | Tessler et al. |
| 3,728,223 A | 4/1973 | Kaneko et al. |
| 4,043,331 A | 8/1977 | Martin et al. |
| 4,205,025 A | 5/1980 | Hart et al. |
| 4,258,134 A | 3/1981 | Yoshida et al. |
| 4,713,448 A | 12/1987 | Balazs et al. |
| 4,761,401 A | 8/1988 | Couchman et al. |
| 4,851,521 A | 7/1989 | Della Valle et al. |
| 4,965,353 A | 10/1990 | Della Valle et al. |
| 5,455,349 A | 10/1995 | Grasshoff et al. |
| 5,462,976 A | 10/1995 | Matsuda et al. |
| 5,520,916 A | 5/1996 | Dorigatti et al. |
| 5,522,879 A | 6/1996 | Scopelianos |
| 5,550,225 A | 8/1996 | Philippe |
| 5,616,568 A | 4/1997 | Pouyani et al. |
| 5,658,582 A | 8/1997 | Dorigatti et al. |
| 5,676,964 A | 10/1997 | Della Valle et al. |
| 5,690,961 A | 11/1997 | Nguyen |
| 5,824,335 A | 10/1998 | Dorigatti et al. |
| 5,868,973 A | 2/1999 | Muller et al. |

(Continued)

FOREIGN PATENT DOCUMENTS

| CA | 2512730 A1 | 7/2004 |
| CH | 628088 A5 | 2/1982 |

(Continued)

OTHER PUBLICATIONS

Xu, Y.-P. et al., "Kinetics of Phenolic Polymerization Catalyzed by Peroxidase in Organic Media," Biotechnology and Bioengineering (1995) 47(1):117-119.

Yamane, Shintaro et al., "Feasibility of chitosan-based hyaluronic acid hybrid biomaterial for a novel scaffold in cartilage tissue engineering," Biomaterials (2005) 26(6);611-619.

Yang, Rui-Meng et al., "Hylauronan-modified superparamagnetic iron oxide nanoparticles for bimodal breast cancer imaging and photothermal therapy," Int'l J. of Nanomedicine 2017: 12, pp. 197-206.

Yao, F. et al., "A Novel Amphoteric, pH-Sensitive, Biodegradable Poly[chitosan-g-(L-lactic-co-citric) acid] Hydrogel," Journal of Applied Polymer Science (2003) 89:3850-3854.

(Continued)

*Primary Examiner* — Jonathan S Lau
*Assistant Examiner* — Everett White
(74) *Attorney, Agent, or Firm* — Wood Herron & Evans LLP

(57) ABSTRACT

The invention discloses a method of preparation of crosslinked materials based on polysaccharides using electromagnetic radiation in an aqueous solution containing a polysaccharide with a bound carbamate photoremovable protecting group (PPG with group —NH—CO—O—) and a polysaccharide containing an aldehyde group —CHO. The crosslinking process itself is carried out by means of a condensation reaction of the photochemically released amino group (—NH₂) with the aldehyde group (—CHO) forming a bond of imine type (—N═CH—). Both processes proceed simultaneously and they can be performed under physiological conditions. The advantage of the suggested solution is the temporal and spatial control of crosslinking that allows the preparation of advanced materials for tissue engineering where the crosslink density and thus the mechanical properties in the material structure can be tailored.

12 Claims, 1 Drawing Sheet

(56) References Cited

U.S. PATENT DOCUMENTS

Figure 1:

| | | |
|---|---|---|
| 6,025,444 A | 2/2000 | Waki et al. |
| 6,075,066 A | 6/2000 | Matsuda et al. |
| 6,162,537 A | 12/2000 | Martin et al. |
| 6,207,134 B1 | 3/2001 | Fahlvik et al. |
| 6,288,043 B1 | 9/2001 | Spiro et al. |
| 6,509,039 B1 | 1/2003 | Nies |
| 6,613,897 B1 | 9/2003 | Yatsuka et al. |
| 6,632,802 B2 | 10/2003 | Bellini et al. |
| 6,641,798 B2 | 11/2003 | Achilefu et al. |
| 6,673,919 B2 | 1/2004 | Yui et al. |
| 6,683,064 B2 | 1/2004 | Thompson et al. |
| 6,719,986 B1 | 4/2004 | Wohlrab et al. |
| 6,902,548 B1 | 6/2005 | Schuler et al. |
| 6,953,784 B2 | 10/2005 | Thompson et al. |
| 7,125,860 B1 | 10/2006 | Renier et al. |
| 7,214,759 B2 | 5/2007 | Pacetti et al. |
| 7,345,117 B1 | 3/2008 | Barbucci et al. |
| 7,550,136 B2 | 6/2009 | Warner et al. |
| 7,680,038 B1 | 3/2010 | Gourlay |
| 7,951,936 B2 | 5/2011 | Sato |
| 8,062,654 B2 | 11/2011 | Nelson et al. |
| 8,129,449 B2 | 3/2012 | Heinzman et al. |
| 8,143,391 B2 | 3/2012 | Yasugi et al. |
| 8,247,546 B2 | 8/2012 | Stucchi et al. |
| 9,017,725 B2 | 4/2015 | Mitra et al. |
| 9,492,586 B2 | 11/2016 | Wolfova et al. |
| 9,522,966 B2 | 12/2016 | Buffa et al. |
| 2002/0016472 A1 | 2/2002 | Tsien et al. |
| 2002/0026039 A1 | 2/2002 | Bellini et al. |
| 2002/0076810 A1 | 6/2002 | Radice et al. |
| 2003/0113354 A1 | 6/2003 | Schmid et al. |
| 2003/0163073 A1 | 8/2003 | Effing et al. |
| 2003/0205839 A1 | 11/2003 | Bachrach |
| 2004/0101546 A1 | 5/2004 | Gorman et al. |
| 2004/0192643 A1 | 9/2004 | Pressato et al. |
| 2005/0112349 A1 | 5/2005 | Laurencin et al. |
| 2005/0118231 A1 | 6/2005 | El Meski et al. |
| 2005/0119219 A1 | 6/2005 | Bellini et al. |
| 2005/0126338 A1 | 6/2005 | Yadav |
| 2005/0266546 A1 | 12/2005 | Warner et al. |
| 2006/0046590 A1 | 3/2006 | Chu et al. |
| 2006/0084759 A1 | 4/2006 | Calabro et al. |
| 2006/0188578 A1 | 8/2006 | Fernandez et al. |
| 2006/0189516 A1 | 8/2006 | Yang et al. |
| 2006/0216324 A1 | 9/2006 | Stucke et al. |
| 2006/0281912 A1 | 12/2006 | James et al. |
| 2007/0149441 A1 | 6/2007 | Aeschlimann et al. |
| 2007/0202084 A1 | 8/2007 | Sadozai et al. |
| 2008/0009630 A1 | 1/2008 | Gao et al. |
| 2008/0063617 A1 | 3/2008 | Abrahams et al. |
| 2008/0071001 A1 | 3/2008 | Sato |
| 2008/0124395 A1 | 5/2008 | Chen et al. |
| 2008/0286300 A1 | 11/2008 | Bardotti et al. |
| 2009/0024019 A1 | 1/2009 | Stein et al. |
| 2009/0028788 A1 | 1/2009 | Achilefu |
| 2009/0180966 A1 | 7/2009 | Borbely et al. |
| 2009/0252810 A1 | 10/2009 | Tommeraas et al. |
| 2010/0002155 A1 | 1/2010 | Yamaguchi et al. |
| 2010/0172892 A1 | 7/2010 | Uvarkina et al. |
| 2010/0207078 A1 | 8/2010 | Marder et al. |
| 2010/0247908 A1 | 9/2010 | Velev et al. |
| 2010/0310631 A1 | 12/2010 | Domard et al. |
| 2010/0310853 A1 | 12/2010 | Schwiegk et al. |
| 2010/0316682 A1 | 12/2010 | Chen et al. |
| 2011/0020917 A1 | 1/2011 | Wen et al. |
| 2011/0028062 A1 | 2/2011 | Chester et al. |
| 2011/0104070 A1 | 5/2011 | Kang et al. |
| 2011/0111012 A1 | 5/2011 | Pepper et al. |
| 2011/0196328 A1 | 8/2011 | Bellini et al. |
| 2011/0200676 A1 | 8/2011 | Lin et al. |
| 2011/0218331 A1 | 9/2011 | Buffa et al. |
| 2011/0229551 A1 | 9/2011 | Doshi et al. |
| 2011/0263724 A1 | 10/2011 | Gurtner et al. |
| 2012/0040463 A1 | 2/2012 | Domard et al. |
| 2012/0095205 A1 | 4/2012 | Buffa et al. |
| 2012/0245323 A1 | 9/2012 | Buffa et al. |
| 2012/0264913 A1 | 10/2012 | Buffa et al. |
| 2012/0277416 A1 | 11/2012 | Carter et al. |
| 2012/0289478 A1 | 11/2012 | Rovati |
| 2013/0017367 A1 | 1/2013 | Ravagnan et al. |
| 2013/0136784 A1 | 5/2013 | Staab |
| 2013/0195791 A1 | 8/2013 | Berkland et al. |
| 2013/0309706 A1 | 11/2013 | Kruglick |
| 2014/0120069 A1 | 5/2014 | Huerta-Angeles et al. |
| 2014/0242145 A1 | 8/2014 | Yoo et al. |
| 2015/0157463 A1 | 6/2015 | Stad et al. |
| 2015/0320873 A1 | 11/2015 | Smejkalova et al. |

FOREIGN PATENT DOCUMENTS

| | | |
|---|---|---|
| CN | 101897976 A | 12/2010 |
| CN | 102154738 A | 8/2011 |
| CN | 103505736 A | 1/2014 |
| CN | 103789874 A | 5/2014 |
| CZ | 2006605 A3 | 4/2008 |
| CZ | 20070299 A3 | 2/2009 |
| CZ | 301899 B6 | 7/2010 |
| CZ | 302503 B6 | 6/2011 |
| CZ | 302504 B6 | 6/2011 |
| CZ | 302856 B6 | 12/2011 |
| CZ | 302994 B6 | 2/2012 |
| CZ | 20101001 A3 | 2/2012 |
| CZ | 303879 B6 | 6/2013 |
| CZ | 304072 B6 | 9/2013 |
| CZ | 20120537 A3 | 3/2014 |
| CZ | 305153 B6 | 5/2015 |
| DE | 10331342 A1 | 2/2005 |
| EP | 0161887 A2 | 11/1985 |
| EP | 0216453 A2 | 4/1987 |
| EP | 0763754 A2 | 3/1997 |
| EP | 0554898 B1 | 5/1997 |
| EP | 1369441 A1 | 12/2003 |
| EP | 1454913 A1 | 9/2004 |
| EP | 1115433 B1 | 12/2004 |
| EP | 1538166 A1 | 6/2005 |
| EP | 1217008 B1 | 3/2006 |
| EP | 1826274 A1 | 8/2007 |
| EP | 1905456 A1 | 4/2008 |
| EP | 1607405 B1 | 5/2011 |
| EP | 2399940 A2 | 12/2011 |
| EP | 2522337 A2 | 11/2012 |
| EP | 2899214 A1 | 7/2015 |
| JP | 62104579 A | 5/1987 |
| JP | 63044883 A | 11/1988 |
| JP | H0214019 A | 1/1990 |
| JP | H0347801 A | 2/1991 |
| JP | 06025306 A | 2/1994 |
| JP | H0625306 A | 2/1994 |
| JP | 3308742 B2 | 7/2002 |
| JP | 2004507586 A | 3/2004 |
| JP | 2004123785 A | 4/2004 |
| JP | 2007262595 A | 10/2007 |
| JP | 2008208480 A | 9/2008 |
| JP | 2008295885 A | 12/2008 |
| KR | 20070118730 A | 12/2007 |
| KR | 20080062092 A | 7/2008 |
| KR | 20080111815 A | 12/2008 |
| KR | 20120118681 A | 10/2012 |
| KR | 20130085294 A | 7/2013 |
| WO | 199311803 A1 | 6/1993 |
| WO | 199627615 A1 | 9/1996 |
| WO | 9637519 A1 | 11/1996 |
| WO | 1996035720 A1 | 11/1996 |
| WO | 199808876 A1 | 3/1998 |
| WO | 199901143 A1 | 1/1999 |
| WO | 199957158 A1 | 11/1999 |
| WO | 0134657 A1 | 5/2001 |
| WO | 0218448 A2 | 3/2002 |
| WO | 0232913 A1 | 4/2002 |
| WO | 2002032285 A2 | 4/2002 |
| WO | 0248197 A1 | 6/2002 |
| WO | 02057210 A1 | 7/2002 |
| WO | 2004061171 A2 | 7/2004 |
| WO | 2005028632 A2 | 3/2005 |

(56) References Cited

FOREIGN PATENT DOCUMENTS

| | | | |
|---|---|---|---|
| WO | 2005092390 A2 | 10/2005 | |
| WO | 2005092929 A1 | 10/2005 | |
| WO | 2006010066 A2 | 1/2006 | |
| WO | 2006026104 A2 | 3/2006 | |
| WO | 2006056204 A1 | 6/2006 | |
| WO | 2006102374 A2 | 9/2006 | |
| WO | 2007003905 A1 | 1/2007 | |
| WO | 2007009728 A2 | 1/2007 | |
| WO | 2007033677 A1 | 3/2007 | |
| WO | 2007101243 A1 | 9/2007 | |
| WO | 2008014787 A1 | 2/2008 | |
| WO | 2008031525 A1 | 3/2008 | |
| WO | 2008077172 A2 | 7/2008 | |
| WO | 2008115799 A1 | 9/2008 | |
| WO | 2009037566 A2 | 3/2009 | |
| WO | 2009050389 A2 | 4/2009 | |
| WO | 2009108100 A1 | 9/2009 | |
| WO | 2009148405 A1 | 12/2009 | |
| WO | 2010018324 A1 | 2/2010 | |
| WO | 2010028025 A1 | 3/2010 | |
| WO | 2010051783 A1 | 5/2010 | |
| WO | 2010061005 A1 | 6/2010 | |
| WO | 2010095049 A1 | 8/2010 | |
| WO | 2010095052 A2 | 8/2010 | |
| WO | 2010095056 A2 | 8/2010 | |
| WO | 2010105582 A1 | 9/2010 | |
| WO | 2010130810 A1 | 11/2010 | |
| WO | 2010138074 A1 | 12/2010 | |
| WO | 2011014432 A1 | 2/2011 | |
| WO | 2011028031 A2 | 3/2011 | |
| WO | 2011059325 A2 | 5/2011 | |
| WO | 2011059326 A2 | 5/2011 | |
| WO | 2011069474 A2 | 6/2011 | |
| WO | 2011069475 A2 | 6/2011 | |
| WO | 2012034544 A2 | 3/2012 | |
| WO | 2012089179 A1 | 7/2012 | |
| WO | 2012146218 A1 | 11/2012 | |
| WO | 2013056312 A1 | 4/2013 | |
| WO | 2013159757 A1 | 10/2013 | |
| WO | 2013167098 A2 | 11/2013 | |
| WO | 2013171764 A2 | 11/2013 | |
| WO | 2014082608 A1 | 6/2014 | |
| WO | 2014082609 A1 | 6/2014 | |
| WO | 2014082611 A1 | 6/2014 | |

OTHER PUBLICATIONS

Ye, Y. et al., "Multivalent Carbocyanine Molecular Probes: Synthesis and Applications," Bioconjugate Chem. 2005, 16, 51-61.
Ye, Y. et al., "Novel Near-Infrared Fluorescent Integrin-Targeted DFO Analogue," Bioconjugate Chem. (2008) 19:225-234.
Ye, Y. et al., "Polyvalent Carbocyanine Molecular Beacons for Molecular Recognitions," J. Am. Chem. Soc. 2004, 126, 7740-7741.
Ye, Y.; et al., "Integrin Targeting for Tumor Optical Imaging," Theranostics 2011, 1, 102-126.
Yeom, J. et al., "Effect of Cross-Linking Reagents for Hyaluronic Acid Hydrogel Dermal Fillers on Tissue Augmentation and Regeneration," Bioconjugate Chemistry (2010) 21(2):240-247.
Zaafarany, I. et al., "Oxidation of Some Sulfated Carbohydrates: Kinetics and Mechanism of Oxidation of Chondroitin-4-Sulfate by Alkaline Permanganate with Novel Synthesis of Coordination Biopolymer Precursor," J. Mat. Sci. Res. (2013) 2(4):23-36.
Zeng, J. et al., "Photo-Induced Solid-State Crosslinking of Electrspun Poly(vinyl alcohol) Fibers," Macromolecular Rapid Communications (2005) 26:1557-1562.
Zeng, Yuan-Xian et al., "Preparation and Enhancement of Thermal Conductivity of Heat Transfer Oil-Based MoS2 Nanofluids," Journal of Nanomaterials, vol. 2013, Art. ID 270490, 6 pgs.
Zhong, S.P. et al., "Biodegradation of hyaluronic acid derivatives by hyalurondiase," Biomaterials (1994) 15(5):359-365.
Zou, X.H. et al., "Specific interactions between human fibroblasts and particular chondroitin sulfate molecules for wound healing," Acta Biomaterialia (2009) 5(5):1588-1595.

Khademhosseini, A. et al., "Layer-by-layer deposition of hyaluronic acid and poly-L-lysine for patterned cell co-cultures," Biomaterials (2004) 25:3583-3592.
Mondek, J. et al., "Thermal degradation of high molar mass hyaluronan in solution and in powder; comparison with BSA," Polymer Degradation and Stability (2015) 120:107-113.
Office Action in U.S. Appl. No. 15/38,078, dated Dec. 21, 2018, 9 pgs.
Office Action in U.S. Appl. No. 15/322,776, dated Dec. 10, 2018, 31 pgs.
Office Action in U.S. Appl. No. 15/737,443 dated Feb. 20, 2019, 13 pgs.
Schachter, D., "The Source of Toxicity in CTAB and CTAB-Stabilized Gold Nanorods," MS thesis submitted to Graduate School-New Brunswick Rutgers, The State University of New Jersey and the Graduate School of Biomedical Sciences, University of Medicine and Dentistry of New Jersey, 2013, 70 pgs.
International Search Report in International Patent Application No. PCT/CZ2010/000030, dated Sep. 1, 2010, 3 pgs.
International Search Report in International Patent Application No. PCT/CZ2010/000128, dated Jun. 9, 2011, 3 pgs.
International Search Report in International Patent Application No. PCT/CZ2010/000129, dated Jun. 15, 2011, 3 pgs.
International Search Report in International Patent Application No. PCT/CZ2011/000126, dated Apr. 12, 2012, 3 pgs.
International Search Report in International Patent Application No. PCT/CZ2012/000035, dated Aug. 28, 2012, 3 pgs.
International Search Report in International Patent Application No. PCT/CZ2013/000023, dated Aug. 9, 2013, 3 pgs.
International Search Report in International Patent Application No. PCT/CZ2013/000057, dated Jul. 24, 2013, 4 pgs.
International Search Report in International Patent Application No. PCT/CZ2013/000063, dated Apr. 23, 2015, 7 pgs.
International Search Report in International Patent Application No. PCT/CZ2013/000091, dated Oct. 31, 2013, 3 pgs.
International Search Report in International Patent Application No. PCT/CZ2013/000116, dated Jan. 28, 2014, 4 pgs.
International Search Report in International Patent Application No. PCT/CZ2013/000155, dated Feb. 19, 2014, 4 pgs.
International Search Report in International Patent Application No. PCT/CZ2013/000156, dated Apr. 4, 2014, 5 pgs.
International Search Report in International Patent Application No. PCT/CZ2013/000157, dated Mar. 19, 2014, 3 pgs.
International Search Report in International Patent Application No. PCT/CZ2013/000158, dated Mar. 19, 2014, 3 pgs.
International Search Report in International Patent Application No. PCT/CZ2014/000138, dated May 4, 2015, 4 pgs.
International Search Report in International Patent Application No. PCT/CZ2015/000018, dated Jul. 22, 2015, 5 pgs.
International Search Report in International Patent Application No. PCT/CZ2016/000071, dated Oct. 10, 2016, 4 pgs.
International Search Report in International Patent Application No. PCT/CZ2016/050036, dated Feb. 6, 2017, 4 pgs.
International Search Report in International Patent Application No. PCT/CZ2016/050048, dated May 3, 2017, 4 pgs.
International Search Report in International Patent Application No. PCT/EP20161064653, dated Aug. 25, 2016, 4 pgs.
Jacoboni, I., "Hyaluronic Acid by Atomic Force Microscopy," Journal of Structural Biology vol. 126, 1999, pp. 52-58.
Jahn, M. et al., "The reaction of hyaluronic acid and its monomers glucuronic acid and N-acetylglucosamine, with reactive oxygen species," Carbohydrate Research, 1999, vol. 321, pp. 228-234.
Japanese Official Action (English language translation) in Japanese Patent Application No. 2012-542355, dated Oct. 17, 2014.
Japanese Official Action (English language translation) in Japanese Patent Application No. 2014-506754, dated Jan. 22, 2015, 2 pgs.
Japanese Official Action (including English language translation) in Japanese Patent Application No. 2012-542356, dated Oct. 3, 2014, 8 pgs.
Ji, Y. et al., "Electrospun three-dimensional hyaluronic acid nanofibrous scaffolds," Biomaterials (2006) 27(1):3782-3792.

(56) References Cited

OTHER PUBLICATIONS

Jia, X.Q. et al., "Synthesis and Characterization of in Situ Cross-Linkable Hyaluronic Acid-Based Hydrogels with Potential Application for Vocal Fold Regeneration," Macromolecules (2004) 37:3239-3248.
Jiang, B. et al., "Study on TEMPO-mediated selective oxidation of hyaluronan and the effects of salt on the reaction kinetics," Carbohydrate Research, Pergamon, GB (2000) 327(4)455-461.
Jin, R. et al., "Enzyme-mediated fast in situ formation of hydrogels from dextran-tyramine conjugates," Biomaterials (2007) 28(18):2791-2800.
Job, D. et al., "Substituent effect on the oxidation of phenols and aromatic amines by horseradish peroxidase compound I," Eur J Biochem 1976, 66 (3), 607-14.
Jou, Chi-Hsiung et al., "Biocompatibility and Antibacterial Activity of Chitosan and Hyaluronic Acid Immobilized Polyester Fibers," Journal of Applied Polymer Science vol. 104, No. 1, 2007, pp. 220-225.
Juhlin, L., "Hyaluronan in skin," Journal of Internal Medicine (1997) 242:61-66.
Kalyanaraman, B. et al., "Peroxidatic oxidation of catecholamines. A kinetic electron spin resonance investigation using the spin stabilization approach" Journal of Biological Chemistry (1984) 259(12) 7584-7589.
Katritzky, A.R. et al., "Cycloaddition Reactions of Heteroaromatic Six-Membered Rings," Chem. Rev. (1989) 89:827-861.
Katz, S.A. et al., "The Toxicology of Chromium with Respect to its Chemical Speciation: a Review," Journal of Applied Toxicology (1993) 13(3):217-224.
Kawaguchi, Y. et al., "The relation between the adsorption behavior at the interface and the conformational changes in hyaluronates partially modified with various acyl chains," Carbohydrate Polymers (1995) 26:149-154.
Kedar, U. et al., "Advances in polymeric micelles for drug delivery and tumor targeting," Nanomedicine: Nanotechnology, Biology, and Medicine (2010) 6(6):714-729.
Khetan, S. et al., "Patterning network structure to spatially control cellular remodeling and stem cell fate within 3-dimensional hydrogels," Biomaterials (2010) 31(32):8228-8234.
Kim, B. et al., "Complexation Phenomena in pH-Responsive Copolymer Networks with Pendent Saccharides," Macromol. (2002) 35:9545-9550.
Kim, T.G. et al., "Controlled Release of Paclitaxel from Heparinized Metal Stent Fabricated by Layer-by-Layer Assembly of Polylysine and Hyaluronic Acid-g-Poly(lactic-co-glycolic acid) Micelles Encapsulating Paclitaxel," Biomacromolecules (2009) 10(6):1532-1539.
Klan, P. et al., "Photoremovable Protecting Groups in Chemistry and Biology: Reaction Mechanisms and Efficacy," Chem. Rev. (2013) 113(1):119-191.
Korsmeyer, R.W. et al., "Mechanisms of solute release from porous hydrophilic polymers," International Journal of Pharmaceutics (1983) 15:25-35.
Kumar, A. et al., "Development of hyaluronic acid-Fe2O3 hybrid magnetic nanoparticles for targeted delivery of peptides," Nanomedicine: Nanotechnology, Biology and Medicine, Elsevier, NL (2007) 3(2)132-137.
Kuo, J.W., "Practical Aspects of Hyaluronan Based Medical Products," 2006, CRC Press, Taylor & Francis Group, pp. 60-61.
Laurent, S. et al., "Magnetic fluid hyperthennia: Focus on superparamagnetic iron oxide nanoparticles," Advances in Colloid and Interface Science (2011) 166:8-23.
Office Action in U.S. Appl. No. 15/038,078, dated Mar. 1, 2018, 10 pgs.
Office Action in U.S. Appl. No. 15/038,078, dated Nov. 3, 2017, 10 pgs.
Office Action in U.S. Appl. No. 15/038,078, dated Sep. 11, 2018, 9 pgs.
Office Action in U.S. Appl. No. 15/124,827, dated Dec. 7, 2017, 9 pgs.
Office Action in U.S. Appl. No. 15/322,776, dated Apr. 17, 2018, 27 pgs.
Office Action in U.S. Appl. No. 15/322,776, dated Jul. 14, 2017, 11 pgs.
Office Action in U.S. Appl. No. 15/322,776, dated Sep. 12, 2017, 23 pgs.
Office Action in U.S. Appl. No. 15/556,370, dated Aug. 2, 2018, 18 pgs.
Office Action in U.S. Appl. No. 15/737,894, dated Oct. 5, 2018, 27 pgs.
Oh, E.J. et al., "Target specific and long-acting delivery of protein, peptide, and nucleotide therapeutics using hyaluronic acid derivatives," J. Controlled Release vol. 141, 2010, pp. 2-12.
Pal, K. et al., "Biopolymers in Controlled-Release Delivery Systems," Modern Biopolymer Science (2009) 519-557.
Park, Y.D. et al., "Photopolymerized hyaluronic acid-based hydrogels and interpenetrating networks," Biomaterials (2003) 24:893-900.
Pasqui, D. et al., "Polysaccharide-Based Hydrogels: The Key Role of Water in Affecting Mechanical Properties," Polymers (2012) 4:1517-1534.
Patel, P.K. et al., "Kinetic studies on the oxidation of phenols by the horseradish peroxidase compound II," Biochim Biophys Acta (1997) 1339(1):79-87.
Perale, G. et al., "Hydrogels in Spinal Cord Injury Repair Strategies," ACS Chem. Neurosci. (2011) 2(7):336-345.
Piggot, A.M. et al., "Synthesis of a new hydrophilic o-nitrobenzyl photocleavable linker suitable for use in chemical proteomics," Tetr. Lett. (2005) 46(47):8241-8244.
Piluso, S. et al., "Hyaluronic acid-based hydrogels crosslinked by copper-catalyzed azide-alkyne cycloaddition with tailorable mechanical properties," International Journal of Artificial Organs (2011) 34:192-197, Abstract.
Prestwich, G.D., "Biomaterials from Chemically-Modified Hyaluronan," internet article, Feb. 26, 2001, 17 pgs.
Prestwich, G.D., "Hyaluronic acid-based clinical biomaterials derived for cell and molecule delivery in regenerative medicine," Journal of Controlled Release (2011) 155:193-199.
Price, Richard D. et al., "Hyaluronic acid: the scientific and clinical evidence," J. Plast. Reconstr. Aesthet. Surg. (2007) 60(10):1110-1119.
Qiu, Y. et al., "Environment-sensitive hydrogels for drug delivery," Advanced Drug Delivery Reviews (2001) 53:321-339.
Rao, K.V.R. et al., "Influence of Molecular Size and Water Solubility of the Solute on its Release from Swelling and Erosion Controlled Polymeric Matrices," Journal of Controlled Release (1990) 12:133-141.
Remy, H., Anorganicka chemie II., Sntl Praha 1971, pp. 306-321.
Ritger, P.L. et al., "A Simple Equation for Description of Solute Release I. Fickian and Non-Fickian Release from Non-Swellable Devices in the Form of Slabs, Spheres, Cylinders or Discs," Journal of Controlled Release (1987) 5:23-36.
Ritger, P.L. et al., "A Simple Equation for Description of Solute Release II. Fickian and Anomalous Release from Swellable Devices," Journal of Controlled Release (1987) 5:37-42.
Rostovtsev, V.V. et al., "A Stepwise Huisgen Cycloaddition Process: Copper(I)-Catalyzed Regioselective 'Ligation' of Azides and Terminal Alkynes," Angew. Chem. Int. Ed. (2002) 41(14):2596-2599.
Rowe et al., "Handbook of Pharmaceutical Excipients," 6th edition, 2009, Pharmaceutical Press, pp. 110-114 and 581-585. (Year: 2009).
Ruoslahti, E. et al., "Targeting of drugs and nanoparticles to tumors," The Journal of Cell Biology (2010) 188(6):759-768.
Rupprecht, A., Wet Spinning of Hyaluronic Acid. Preparation of Oriented Samples; Acta Chemica Scandinavica; 1979; 33; 779-780.
Saettone et al., "Evaluation of muco-adhesive properties and in vivo activity of ophthalmic vehicles based on hyaluronic acid," 1989, International Journal of Pharmaceutics, vol. 51, pp. 203-212. (Year: 1989).
Sahiner, N. et al., "Fabrication and characterization of cross-linkable hydrogel particles based on hyaluronic acid: potential application in volcal fold regeneration", Journal of Biomaterials Science, Polymer Edition, vol. 19, Issue 2, pp. 223-243.

(56) References Cited

OTHER PUBLICATIONS

Schante, C.E. et al., "Chemical modifications of hyaluronic acid for the synthesis of derivatives for a broad range of biomedical applications," Carbohydrate Polymers (2011) 85:469-489.

Scott, J.E. et al., "Periodate Oxidation of Acid Polysaccharides", Histochemie, Apr. 26, 1969, vol. 19, pp. 155-161.

Scott, J.E. et al., "Secondary and tertiary structures of hyaluronan in aqueous solution, investigated by rotary shadowing—electron microscopy and computer simulation," J. Biochem vol. 274, 1991, pp. 699-705.

Sedova, P. et al., "Preparation of hyaluronan polyaldehyde—a precursor of biopolymer conjugates," Carbohydrate Research (2013) 371:8-15.

Seidlits, S.K. et al., "The effects of hyaluronic acid hydrogels with tunable mechanical properties on neural progenitor cell differentiation" Biomaterials (2010) 31:3930-3940.

Shang, J. et al., "Chitosan-based electroactive hydrogel," Polymer (2008) 49:5520-5525.

Sheehan, J.K. et al., "X-ray Diffraction Studies on the Connective Tissue Polysaccharides," J. Mol. Biol. (1975) 91:153-163.

Shen, Yan et al., "Synthesis and characterization of low molecular weight hyaluronic acid-based cationic micelles for efficient siRNA delivery," Carbohydrate Polymers (2009) 77(1):95-104.

Shen, Yi et al., "Synthesis, Characterization, Antibacterial and Antifungal Evaluation of Novel Monosaccharide Esters," Molecules (2012) 17(7):8661-8673.

Shimizu, M. et al., "Studies on hyaluronidase, chondroitin sulphatase, proteinase and phospholipase secreted by Candida species", MYCOSES (1996) 39:161-167.

Shutava, T. et al., "Microcapsule Modification with Peroxidase-Catalyzed Phenol Polymerization," Biomacromolecules (2004) 5(3):914-921.

Sieburth, S.M. et al., "Fusicoccin Ring System by [4+4} Cycloaddition. 2. A Model Study," Tetrahedron Letters (1999) 40:4007-4010.

Sieburth, S.M. et al., "The [4+4] Cycloaddition and its Strategic Application in Natural Product Synthesis," Tetrahedron (1996) 52(18):6251-6282.

Slaughter, B.V. et al., "Hydrogels in Regenerative Medicine," Advanced Materials (2009) 21(32-33):3307-3329.

Smeds, K.A. et al., "Photocrosslinkable polysaccharides for in situ hydrogel formation," J. Biomed. Mater. Res. (2001) 54:115-121.

Smejkalova, D. et al., "Structural and conformational differences of acylated hyaluronan modified in protic and aprotic solvent system," Carbohydrate Polymers (2012) 87(2):1460-1466.

Staskus, P.W. et al., "Double-Stranded Structure for Hyaluronic Acid in Ethanol-Aqueous Solution as Revealed by Circular Dichroism of Oligomers," Biochemistry vol. 27, No. 5, 1988, pp. 1528-1534.

Su, W.Y. et al., "Injectable oxidized hyaluronic acid/adipic acid dihydrazide hydrogel for nucleus pulposus regeneration," Acta. Biomater. (2010) 6(8):3044-3055.

Bobula, T. et al., "One-pot synthesis of alpha,beta-unsaturated polyaldehyde of chondroitin sulfate," Carbohydrate Polymers (2016) 136:1002-1009.

Bobula, T. et al., "Solid-state photocrosslinking of hyaluronan microfibres," Carbohydrate Polymers (2015) 125:153-160.

Brand-Williams, W. et al., "Use of a Free Radical Method to Evaluate Antioxidant Activity," LWT—Food Science and Technology (1995) 28:25-30.

Collins, M. N. et al., "Hyaluronic Acid Based Scaffolds for Tissue Engineering—A review," Carbohydrate Polymers (2013) 92:1262-1279.

Hacker, M. C. et al., "Multi-Functional Macromers for Hydrogel Design in Biomedical Engineering and Regenerative Medicine," Inter. J. of Mol. Sc. (2015) 16:27677-27706.

Horton, D. et al., "Synthethis of 2,3-Unsaturated Polysaccharides From Amylose and Xylan," Carbohydrate Research (1975) 40:345-352.

International Search Report in International Patent Application No. PCT/CZ2017/050026, dated Oct. 26, 2017, 2 pgs.

Kelly, S. J. et al., "Kinetic properties of Streptococcus pneumoniae hyaluronate lyase," Glycobiology (2001) 11(4):297-304.

Khetan, S. et al., "Sequential crosslinking to control cellular spreading in 3-dimensional hydrogels," Soft Matter (2009) 5:1601-1606.

Kühn, A. V. et al., "Identification of hyaluronic acid oligosaccharides by direct coupling of capillary electrophoresis with electrospray ion trap mass spectrometry," Rapid Communications in Mass Spectrometry (2003) 17:576-582.

Mero, A. et al., "Hyaluronic Acid Bioconjugates for the Delivery of Bioactive Molecules," Polymers (2014) 6(2):346-369.

Nimmo, C. M. et al., "Diels-Alder Click Cross-Linked Hyaluronic Acid Hydrogels for Tissue Engineering," Biomacromolecules (2011) 12:824-830.

Vigo, T. L. et al., "Deoxycelluloses and Related Structures," Polymers for Advanced Technologies (1999) 10:311-320.

Written Opinion in International Patent Application No. PCT/CZ2017/050026, dated Oct. 26, 2017, 5 pgs.

Dawlee, S. et al., "Oxidized Chondroitin Sulfate-Cross-Linked Gelatin Matrixes: A New Class of Hydrogels," Biomacromolecules (2005) 6(4):2040-2048.

De Figueiredo, R.M. et al., "N,N'-Carbonyldiimidazole-Mediated Cyclization of Amino Alcohols to Substituted Azetidines and Other N-Heterocycles," J. Org. Chem. (2006) 71(11):4147-4154.

Dilling, W.L. et al., "Organic Photochemistry. XII. The Photodimerization and Photoisomerization of 2-Pyridone and Its Monochloro Derivatives," Mol. Photochem. (1973) 5(4):371-409.

Ding, B. et al., "TEMPO-mediated selective oxidation of substituted polysaccharides—an efficient approach for the determination of the degree of substitution at C-6," Carbohydrate Research (2008) 343(18)3112-3116.

Donati, A. et al., "Solution Structure of Hyaluronic Acid Oligomers by Experimental and Theoretical NMR, and Molecular Dynamics Simulation," Biopolymers (2001) 59:434-445.

Dumitriu, S., "Characterization and Properties of Hyaluronic Acid (Hyaluronan)," by M. Milas et al., Chap. 22 of Polysaccharides: Structural Diversity and Functional Versatility, 1998, Marcel Dekker Inc., pp. 535-549.

Duncan, R. et al., "Nanomedicine(s) under the Microscope," Molecular Pharmaceutics (2011) 8(6):2101-2141.

Dunford, H. B. et al., "Kinetics of the oxidation of p-aminobenzoic acid catalyzed by horseradish peroxidase compounds I and II," J Biol Chem 1975, 250(8), 2920-32.

Eenschooten, C. et al., "Preparation and structural characterisation of novel and versatile amphiphilic octenyl succinic anhydride-modified hyaluronic acid derivatives," Carbohydrate Polymers (2010) 79(3):597-605.

El-Dakdouki, M.H. et al., "Development of drug loaded nanoparticles for tumor targeting. Part 1: synthesis, characterization, and biological evaluation in 2D cell cultures," Nanoscale (2013) 5(9):3895-3903.

El-Dakdouki, M.H. et al., "Development of Multifunctional Hyaluronan-Coated Nanoparticles for Imaging and Drug Delivery to Cancer Cells," Biomacromolecules (2012) 13(4):1144-1151.

El-Sherbiny, I.M. et al., "Poly(ethylene glycol)-carboxymethyl chitosan-based pH-responsive hydrogels: photo-induced synthesis, characterization, swelling, and in vitro evaluation as potential drug carriers," Carbohydrate Research (2010) 345:2004-2012.

Elander, R.P., "Industrial production of β-lactam antibiotics," Applied Microbiology and Biotechnology (2003) 61:385-392.

European First Official Action in European Patent Application No. 10812840.6-1306, dated Jul. 2, 2013, 4 pgs.

European Second Official Action in European Patent Application No. 10812840.6-1306, dated Sep. 24, 2014, 5 pgs.

Feng, Qian et al., "Self-Assembly Behaviour of Hyaluronic Acid on Mica by Atomic Force Microscopy," vol. 20, No. 1, 2004, pp. 146-148 and 152 (English language Abstract p. 152).

Ferrero, C. et al., "Fronts movement as a useful tool for hydrophilic matrix release mechanism elucidation," International Journal of Pharmaceutics (2000) 202:21-28.

(56) References Cited

OTHER PUBLICATIONS

Ferruti, P. et al., "Novel Poly(amido-amine)-Based Hydrogels as Scaffolds for Tissue Engineering," Macromol. Biosci. (2005) 5:613-622.
Fleige, E. et al., "Stimuli-responsive polymeric nanocarriers for the controlled transport of active compounds: Concepts and applications," Advanced Drug Delivery Reviews (2012) 64(9):866-884.
Funakoshi, T. et al., "Novel chitosan-based hyaluronan hybrid polymer fibers as a scaffold in ligament tissue engineering," Journal of Biomedical Materials Reasearch, Part A, vol. 74A, No. 3, 2005, pp. 338-346.
Furuta, T. et al., "Anthraquinon-2-ylmethoxycarbonyl (Aqmoc): A New Photochemically Removable Protecting Group for Alcohols," Org. Lett. (2001) 3(12):1809-1812.
Ghan, R. et al., "Enzyme-Catalyzed Polymerization of Phenols within Polyelectrolyte Microcapsules," Macromolecules (2004) 37(12), 4519-4524.
Gibby, W.A., "Cross-Linked DTPA Polysaccharides for Magnetic Resonance Imaging, Synthesis and Relaxation Properties," Invest. Radiol. 1989, vol. 24, pp. 302-309.
Gilabert, W.A. et al., "Differential substrate behaviour of phenol and aniline derivatives during oxidation by horseradish peroxidase: kinetic evidence for a two-step mechanism," Biochim. Biophys. Acta. (2004) 1699:235-243.
Gilabert, M.A. et al., "Kinetic characterization of phenol and aniline derivates as substrates of peroxidase," Biol. Chem. (2004) 385(9):795-800.
Gilabert, M.A. et al., "Stereospecificity of horseradish peroxidase," Biol. Chem. (2004) 385:1177-1184.
Gobouri, A.A. et al., "Novel Synthesis of Diketo-Acid Chondroitin-4-sulfate as Coordination Biopolymer Precursor through Oxidation of Chondroitin-4-sulfate by Alkaline Permanganate," International Journal of Sciences (2013) 7:1-11.
Godula, K. et al., "Synthesis of Glycopolymers for Microarray Applications via Ligation of Reducing Sugars to a Poly (acryloyl hydrazide) Scaffold," J. Am. Chem. Soc. (2010) 132:9963-9965.
Gong, J. et al., "Polymeric, micelles drug delivery system in oncology," Journal of Controlled Release (2012) 159(3):312-323.
Green, T.W. et al., "Protective Groups in Organic Synthesis," 1999, New York: John Wiley & Sons, 3rd ed., Chap. 1, pp. 1-16.
Guillaumie, F. et al., "Comparative studies of various hyaluronic acids produced by microbial fermentation for potential topical ophthalmic applications," Journal of Biomedical Materials Research Part A (2009) 1421-1430.
Gupta, P. et al., "Hydrogels: from controlled release to pH-responsive drug delivery," Drug Discovery Today (2002) 7(10):569-579.
Hasegawa, T. et al., "'Click chemistry' on polysaccharides: a convenient, general, and monitorable approach to develop (1-3)-β-D-glucans with various functional appendages," Carbohydrate Research (2006) 341:35-40.
Hewson, W. D. et al., "Oxidation of p-cresol by horseradish peroxidase compound I," J Biol Chem 1976, 251 (19), 6036-42.
Hewson, W. D. et al., "Stoichiometry of the reaction between horseradish peroxidase and p-cresol," J Biol Chem 1976, 251(19), 6043-52.
Higashimura, H. et al., Oxidative Polymerization. John Wiley & Sons, Inc. Olefin Fibers (2002) 10:740-764.
Hill, T. K. et al., "Indocyanine Green-Loaded Nanoparticles for Image-Guided Tumor Surgery," Bioconjugate Chem. (2015) 26:294-303.
Hoffman, A.S., "'Intelligent' Polymers in Medicine and Biotechnology," Artificial Organs (1995) 19(5):458-467.
Holten, K.B. et al., "Appropriate Prescribing of Oral Beta-Lactam Antibiotics," American Family Physician (2000) 62(3):611-620.
Huang, L. et al., "A Facile Method for Oxidation of Primary Alcohols to Caroxylic Acids and Its Application in Glycosaminoglycan Syntheses," Chemistry (2006) 12(20):5246-5252.
Huerta-Angeles, G. et al., "Synthesis of highly substituted amide hyaluronan derivatives with tailored degree of substitution and their crosslinking via click chemistry," Carbohydrate Polymers (2011) 84:1293-1300.
Huh, K.M. et al., "Hydrotropic polymer micelle system for delivery of paclitaxel," Journal of Controlled Release (2005) 101:59-68.
Hynes, W.L. et al., "Hyaluronidases of Gram-positive bacteria," FEMS Microbiology Letters (2000) 183:201-207.
Inanaga, J. et al., "A Rapid Esterification by Means of Mixed Anhydride and Its Application to Large-ring Lactonization," Bulletin of the Chemical Society of Japan (1979) 52(7):1989-1993.
International Preliminary Report on Patentability in International Patent Application No. PCT/CZ2010/000128, dated Feb. 5, 2013, 5 pgs.
International Preliminary Report on Patentability in International Patent Application No. PCT/CZ2010/000129, dated Jun. 12, 2012, 5 pgs.
Balan, V. et al., "Strategies to improve chitosan hemocompatibility: A review," European Polymer Journal (2004) 53:171-188.
Choi, W. II et al., Targeted antitumor efficacy and imaging via multifunctional nano-carrier conjugated with anti-HER2 trastuzumab, Nanomedicine: Nanotechnology, Biology, and Medicine (2015) 11:359-368.
Frangioni, J. V., "In vivo near-infrared fluorescence imaging," Curr. Opin. Chem. Biol. (2003) 7(5):626-634.
Funfstuck, V. V. et al., "Kontaktallergie gegenuber Dicyclohexylcarbodiimid," Dermatosen (1986) 34(4):110-111.
Huerta-Angeles, G. et al., "Novel synthetic method for the preparation of amphiphilic hyaluronan by means of aliphatic aromatic anhydrides," Carbohydrate Polymers (2014) 111:883-891.
Hussain, M. A. et al., "Acylation of Cellulose with N,N'-Carbonyldiimidazole-Activated Acids in the Novel Solvent Dimethyl Sulfoxide/Tetrabutylammonium Fluoride," Macromol. Rapid Commun. (2004) 25:916-920.
Kobayashi, H. et al., "New Strategies for Fluorescent Probe Design in Medical Diagnostic Imaging," Chem. Rev. (2010) 110(5):2620-2640.
Kokuryo, D. et al., "Corrigendum to SPIO-PICsome: Development of a highly sensitive and stealth-capable MRI nano-agent for tumor detection using SPIO-loaded unimellar polyion complex vesicles (PICsomes)," Journal of Controlled Release (2014) 178:125.
Lee, Dong-Eun et al., "Hyaluronidase-Sensitive SPIONs for MR/Optical Dual Imaging Nanoprobes," Marcomol. Res. (2011) 19(8):861-867.
Leach, J.B. et al., "Characterization of protein release from photocrosslinkable hyaluronic acid-polyethylene glycol hydrogel tissue engineering scaffolds," Biomaterials (2005) 26:125-135.
Leach, J.B. et al., "Photocrosslinked Hyaluronic Acid Hydrogels: Natural, Biodegradable Tissue Engineering Scaffolds," Biotechnol Bioeng. (2003) 82:578-589.
Lee, Dong-Eun et al., "Amphiphilic hyaluronic acid-based nanoparticles for tumor-specific optical/MR dual imaging," Journal of Materials Chemistry (2012) 22(1):10444-10447.
Lee, F. et al., "An injectable enzymatically crosslinked hyaluronic acid-tyramine hydrogel system with independent tuning of mechanical strength and gelation rate," Soft Matter (2008) 4:880-887.
Lee, F. et al., "An injectable hyaluronic acid-tyramine hydrogel system for protein delivery," Journal of Controlled Release (2009) 134:186-193.
Lee, K.Y. et al., "Electrospinning of polysaccharides for regenerative medicine," Advanced Drug Delivery Reviews (2009) 61:1020-1032.
Lee, S.A. et al., "Spectroscopic studies of the physical properties of hyaluronate films: the origin of the phase transition," Carbohydrate Polymers (1995) 28:61-67.
Lee, Yuhan et al., "Bioinspired Surface Immobilization of Hyaluronic Acid on Monodisperse Magnetite Nanocrystals for Targeted Cancer Imaging," Advanced Materials (2008) 20:4154-4157.
Li, J. et al., "Electrospinning of Hyaluronic Acid (HA) and HA/Gelatin Blends," Macromolecular Rapid Communications (2006) 27:114-120.

(56) References Cited

OTHER PUBLICATIONS

Li, J. et al., "Redox-sensitive micelles self-assembled from amphiphilic hyaluronic acid-deoxycholic acid conjugates for targeted intracellular delivery of paclitaxel," Biomaterials (2012) 33(7), 2310-2320.
Li, M. et al., Comparison of Two Ultrasmall Superparamagnetic Iron Oxides on Cytotoxicity and MR Imaging of Tumors, Theranostics (2012) 2(1):76-85.
Liang, Y. et al., "An in situ formed biodegradable hydrogel for reconstruction of the corneal endothelium," Colloids and Surfaces B: Biointerfaces (2011) 82(1):1-7.
Linhardt, R.J. et al., "Polysaccharide lyases," Applied Biochemistry and Biotechnology (1986) 12:135-176.
Liu, Yanchun et al., "Biocompatibility and stability of disulfide-crosslinked hyaluronan films," Biomaterials (2005) 26 (23):4737-4746.
Liu, Yanhua et al., "Dual targeting folate-conjugated hyaluronic acid polymeric micelles for paclitaxel delivery," International Journal of Pharmaceutics (2011) 421(1):160-169.
Luo, S. et al., "A review of NIR dyes in cancer targeting and imaging," Biomaterials (2011) 32:7127-7138.
Luo, Yanfeng et al., "Novel amphoteric pH-sensitive hydrogels derived from ethylenediaminetetraacetic dianhydride, butanediamine and amino-terminated poly(ethylene glycol): Design, synthesis and swelling behavior," European Polymer Journal (2011) 47:40-47.
Maeda, H., "The Enhanced Permeability and Retention (EPR) Effect in Tumor Vasculature: The Key Role of Tumor-Selective Macromolecular Drug Targeting," Advances in Enzyme Regulation (2001) 41(1):189-207.
Malkoch, M. et al., "Synthesis of well-defined hydrogel networks using Click chemistry," Chem. Commun. (2006) 2774-2776.
Marega, R. et al., "Hyaluronan-Carbon Nanotube Derivatives: Synthesis, Conjugation with Model Drugs, and DOSY NMR Characterization," Eur. J. Org. Chem. (2011) 28:5617-5625.
Matsushima, R. et al., "Photoreactions of Alkylated 2-Pyridones," J. Chem. Soc. Perkin Trans. 2 (1985) 1445-1448.
Mayol, L. et al., "Amphiphilic hyaluronic acid derivatives toward the design of micelles for the sustained delivery of hydrophobic drugs," Carbohydrate Polymers (2014) 102:110-116.
Mazzone, S.B., "Fluorescent styryl dyes FM 1-43 and FM2-10 are muscarinic receptor antagonists: intravital visualization of receptor occupancy," The Journal of Physiology (2006) 575(1):23-35.
McIntyre, J.E, "The Chemistry of Fibres," Studies in Chemistry No. 6, 1971, p. 15.
McTaggart, L.E. et al., "Assessment of polysaccharide gels as drug delivery vehicles," Int. J. Pharm. 1993, vol. 100, pp. 199-206.
Merriam Webster Online Dictionary, obtained online at: http://www.merriam-webster.com/cgi-bin/dictionary?book=Dictionary&va=derivative, downloaded on Jul. 5, 2008.
Miki, K. et al., "Near-Infrared Dye-Conjugated Amphiphilic Hyaluronic Acid Derivatives as a Dual Contrast Agent for In Vivo Optical and Photoacoustic Tumor Imaging," Biomacromolecules (2015) 16:219-227.
Miller, R.J. et al., Chemistry and Biology of Hyaluronan : Medicinal Uses of Modified Hyaluronate. Elsevier Ltd. 2004. 505-528.
Nevell, T.P. et al., "Cellulose Chemistry and its Applications," 1985, John Wiley & Sons, pp. 455-479.
Normandin, L. et al., "Manganese Neurotoxicity: An Update of Pathophysiologic Mechanisms," Metab Brain Dis (2002) 17(4):375-387.
Office Action in U.S. Appl. No. 13/512,484, dated May 11, 2016, 8 pgs.
Office Action in U.S. Appl. No. 13/512,484, dated Oct. 1, 2015, 8 pgs.
Office Action in U.S. Appl. No. 13/512,484, dated Sep. 11, 2014, 8 pgs.
Office Action in U.S. Appl. No. 13/514,759, dated Jul. 30, 2015, 12 pgs.
Office Action in U.S. Appl. No. 13/514,759, dated Sep. 24, 2014, 10 pgs.
Office Action in U.S. Appl. No. 13/977,181, dated Jan. 22, 2016, 8 pgs.
Office Action in U.S. Appl. No. 14/113,527, dated Feb. 12, 2016, 11 pgs.
Office Action in U.S. Appl. No. 14/113,527, dated Sep. 8, 2016, 10 pgs.
Office Action in U.S. Appl. No. 14/395,575, dated Jul. 6, 2017, 9 pgs.
Office Action in U.S. Appl. No. 14/420,012, dated Jun. 16, 2016, 6 pgs.
Office Action in U.S. Appl. No. 14/430,731, dated May 19, 2016, 12 pgs.
Office Action in U.S. Appl. No. 14/647,185, dated Sep. 28, 2016, 5 pgs.
Office Action in U.S. Appl. No. 14/647,626, dated Feb. 17, 2017, 12 pgs.
Office Action in U.S. Appl. No. 14/647,626, dated Jul. 28, 2016, 35 pgs.
Office Action in U.S. Appl. No. 14/647,626, dated Jun. 16, 2017, 14 pgs.
Office Action in U.S. Appl. No. 14/647,626, dated Nov. 13, 2017, 18 pgs.
Office Action in U.S. Appl. No. 14/647,649, dated Apr. 19, 2018, 9 pgs.
Office Action in U.S. Appl. No. 14/647,649, dated Dec. 8, 2017, 9 pgs.
Office Action in U.S. Appl. No. 14/647,649, dated May 31, 2017, 11 pgs.
Svanovsky, E. et al., "The effect of molecular weight on the biodistribution of hyaluronic acid radiolabeled with 111-In after intravenous administration to rats," Eur. J. Drug Metab. Ph. 2008, vol. 33, No. 3, pp. 149-157.
Tan, H. et al., "Injectable in situ forming biodegradable chitosan-hyaluronic acid based hydrogels for cartilage tissue engineering," Biomaterials (2009) 30(13):2499-2506.
Tan, X. et al., "A NIR heptamethine dye with intrinsic cancer targeting, imaging and photosensitizing propeties," Biomaterials (2012) 33:2230-2239.
Tankam, P.F. et al., "Alkynyl polysaccharides: synthesis of propargyl potato starch followed by subsequent derivatizations," Carbohydrate Research (2007) 342:2049-2060.
Tao, Y. et al., "Core cross-linked hyaluronan-styrylpyridinium micelles as a novel carrier for paclitaxel," Carbohydrate Polymers (2012) 88(1):118-124.
Testa, G. et al., "Influence of dialkyne structure on the properties of new click-gels based on hyaluronic acid," International Journal of Pharmaceutics (2009) 378:86-92.
Thakar, D. et al., "A quartz crystal microbalance method to study the terminal functionalization of glycosaminoglycans," Chemical Communications (2014) 50(96):15148-15151.
Thelin, M. et al., "Biological functions of iduronic acid in chondroitin/dermatan sulfate," FEBS Journal (2013) 280:2431-2446.
Thomas et al, "Hyaluronic acid conjugated superparamagnetic iron oxide nanoparticle for cancer diagnosis and hyperthermia therapy," Carbohydrate Polymers 131 (2015) pp. 439-446.
Til, H.P. et al., "Acute and Subacute Toxicity of Tyramine, Spennidine, Spennine, Putrescine and Cadaverine in Rats," Food and Chemical Toxicology (1997) 35(3-4):337-348.
Tonelli, A.E., "Effects of crosslink density and length on the number of intramolecular crosslinks (defects) introduced into a rubbery network," Polymer (1974) 15(4):194-196.
Tornoe, C. et al. "Peptidotriazoles on Solid Phase: [1,2,3]-Triazoles by Regiospecific Copper(I)-Catalyzed 1,3-Dipolar Cycloadditions of Terminal Alkynes to Azides," J. Org. Chem. (2002) 67:3057-3064.
Um, I.C. et al., "Electro-Spinning and Electro-Blowing of Hyaluronic Acid," Biomacromolecules (2004) 5:1428-1436.
Uyama, H. et al., "Enzymatic Synthesis of Polyphenols," Current Organic Chemistry (2003) 7:1387-1397.
Van Bommel, K.J.C. et al., "Responsive Cyclohexane-Based Low-Molecular-Weight Hydrogelators with Modular Architecture," Angew. Chem. Int. Ed. (2004) 1663-1667.

(56) References Cited

OTHER PUBLICATIONS

Veitch, N.C., "Horseradish peroxidase: a modem view of a classic enzyme," Phytochemistry (2004) 65:249-259.
Wang, J. et al., "Polymeric Micelles for Delivery of Poorly Soluble Drugs: Preparation and Anticancer Activity In Vitro of Paclitaxel Incorporated into Mixed Micelles Based on Poly(ethylene Glycol)-Lipid Conjugate and Positively Charged Lipids," Journal of Drug Targeting (2005) 13(1), 73-80.
Wang, W. et al., "Developing Fluorescent Hyaluronan Analogs for Hyaluronan Studies," Molecules 2012, 17, 1520-1534.
Wang, X. et al., "Formation of water-resistant hyaluronic acid nanofibers by blowing-assisted electro-spinning and non-toxic post treatments," Polymer (2005) 46:4853-4867.
Weng L., et al., "Self-crosslinkable hydrogels composed of partially oxidized hyaluronan and gelatin: In vitro and in vivo responses," Journal of Biomedical Materials Research Part A, 85:352-365.
Weng, L. et al., "In vitro and in vivo suppression of cellular activity by guanidinoethyl disulfied released from hydrogel microspheres composed of partially oxidized hyaluronan and gelatin", Biomaterials, Aug. 3, 2008, vol. 29, pp. 4149-4156.
Weng, L. et al., "Self-crosslinkable hydrogels composed of partially oxidized hyaluronan and gelatin: In vitro and in Vivo responses," Journal of Biomedical Materials Research Part A, Aug. 9, 2007, pp. 352-365.
Wermuth, C.G., "Similarity in drugs: reflections on analogue design," Drug Discovery Today (2006) 11(7/8):348-354.
Werner, T. et al., "Simple Method for the Preparation of Esters from Grignard Reagents and Alkyl 1-Imidazolecarboxylates," J. Org. Chem. (2006) 71(11):4302-4304.
Won, K. et al., "Horseradish Peroxidase-Catalyzed Polymerization of Cardanol in the Presence of Redox Mediators," Biomacromolecules (2003) 5(1), 1-4.
Wondraczek, H. et al., "Synthesis of highly functionalized dextran alkyl carbonates showing nanosphere formation," Carbohydrate Polymers (2011) 83:1112-1118.
Written Opinion in International Patent Application No. PCT/CZ2009/000131, dated Apr. 9, 2010, 3 pgs.
Written Opinion in International Patent Application No. PCT/CZ2010/000030, dated Sep. 1, 2010, 4 pgs.
Written Opinion in International Patent Application No. PCT/CZ2010/000128, dated Jun. 9, 2011, 4 pgs.
Written Opinion in International Patent Application No. PCT/CZ2010/000129, dated Jun. 15, 2011, 4 pgs.
Written Opinion in International Patent Application No. PCT/CZ2011/000126, dated Apr. 12, 2012, 4 pgs.
Written Opinion in International Patent Application No. PCT/CZ2012/000035, dated Aug. 28, 2012, 4 pgs.
Written Opinion in International Patent Application No. PCT/CZ2013/000023, dated Aug. 9, 2013, 3 pgs.
Written Opinion in International Patent Application No. PCT/CZ2013/000057, dated Jul. 24, 2013, 4 pgs.
Written Opinion in International Patent Application No. PCT/CZ2013/000063, dated Apr. 23, 2015, 9 pgs.
Written Opinion in International Patent Application No. PCT/CZ2013/000091, dated Oct. 31, 2013, 4 pgs.
Written Opinion in International Patent Application No. PCT/CZ2013/000116, dated Jan. 28, 2014, 5 pgs.
Written Opinion in International Patent Application No. PCT/CZ2013/000155, dated Feb. 19, 2014, 6 pgs.
Written Opinion in International Patent Application No. PCT/CZ2013/000156, dated Apr. 4, 2014, 7 pgs.
Written Opinion in International Patent Application No. PCT/CZ2013/000157, dated Mar. 19, 2014, 6 pgs.
Written Opinion in International Patent Application No. PCT/CZ2013/000158, dated Mar. 19, 2014, 7 pgs.
Written Opinion in International Patent Application No. PCT/CZ2014/000138, dated May 4, 2015, 5 pgs.
Written Opinion in International Patent Application No. PCT/CZ2015/000018, dated Jul. 22, 2015, 8 pgs.
Written Opinion in International Patent Application No. PCT/CZ2015/000068, dated Jan. 8, 2016, 6 pgs.
Written Opinion in International Patent Application No. PCT/CZ2016/000027, dated Jun. 27, 2016, 6 pgs.
Written Opinion in International Patent Application No. PCT/CZ2016/000071, dated Oct. 10, 2016, 5 pgs.
Written Opinion in International Patent Application No. PCT/CZ2016/050036, dated Feb. 6, 2017, 6 pgs.
Written Opinion in International Patent Application No. PCT/CZ2016/050048, dated May 3, 2017, 6 pgs.
Written Opinion in International Patent Application No. PCT/EP2016/064653, dated Aug. 25, 2016, 6 pgs.
Xu, Y. et al., "Feasibility study of a novel crosslinking reagent (alginate dialdehyde) for biological tissue fixation," Carbohydrate Polymers (2012) 87(2):1589-1595.
Akkara, J.A. et al., "Synthesis and Characterization of Polymers Produced by Horseradish Peroxidase in Dioxane," Journal of Polymer Science Part A: Polymer Chemistry (1991) 29(11):1561-1574.
Angelin, M. et al., "Direct, Mild, and Selective Synthesis of Unprotected Dialdo-Glycosides," European Journal of Organic Chemistry (2006):4323-4326.
Armstrong, D.C. et al., "Culture Conditions Affect the Molecular Weight Properties of Hyaluronic Acid Produced by *Streptococcus zooepidemicus*," Appl. Environ. Microbiol. (1997) 63(7):2759-2764.
Atkins, E.D.T. et al., "The Conformation of the Mucopolysaccharides," J. Biochem. (1972) 128:1255-1263.
Baeurle, S.A. et al., "Effect of the counterion behavior on the frictional-compressive properties of chondroitin sulfate solulions," Polymer (2009) 50(7):1805-1813.
Baijal, K. P. et al., "Tumor-enhancing effects of cholic acid are exerted on the early stages of colon carcinogenesis via induction of aberrant crypt foci with an enhanced growth phenotype," Canadian Journal of Physiology and Pharmacology, 1998, 76(12), 1095-1102.
Bakke, M. et al., "Identification, characterization, and molecular cloning of a novel hyaluronidase, a member of glycosyl hydrolase family 16, from *Penicillium* spp.," FEBS Letters (2011) 585(1):115-120.
Banerji, S. et al., "Structures of the Cd44-hyaluronan complex provide insight into a fundamental carbohydrate-protein interaction," Nature structural and molecular biology (2007) 14:234-239.
Benedetti, L. et al., "Biocompatibility and biodegradation of different hyaluronan derivatives (Hyaff) implanted-in rats," Biomaterials (1993) 14(15):1154-1160.
Bezakova, Z. et al., "Effect of microwave irradiation on the molecular and structural properties of hyaluronan," Carbohydrate Polymers (2008) 73(4):640-646.
Bottegoni, C. et al., "Oral chondroprotection with nutraceuticals made of chondroitin sulphate plus glucosamine sulphate in osteoarthritis," Carb. Pol. (2014) 109:126-138.
Boyer, I.J., "Toxicity of dibutyltin, tributyltin and other organotin compounds to humans and to experimental animals," Toxicology (1989) 55(3), 253-298.
Breunig, M. et al., "Breaking up the correlation between efficacy and toxicity for nonviral gene delivery," PNAS (2007) 104(36):14454-14459.
Buffa, R. et al., "Branched hyaluronic acid, synthesis, analysis and biological properties," Journal of Tissue Engineering and Regenerative Medicine (2014) 8(1):321.
Buffa, R. et al., "New method of immobilization of hyaluronic acid oligomers," Journal of Tissue Engineering and Regenerative Medicine (2014) 8(1):321-322.
Burdick, J.A. et al., "Controlled Degradation and Mechanical Behavior of Photopolymerized Hyaluronic Acid Networks," Biomacromolecules (2005) 6:386-391.
Burdick, J.A. et al., "Hyaluronic Acid Hydrogels for Biomedical Applications," Adv. Mater. (2011) 23:H41-H56.
Burke, J., Solubility Parameters: Theory and Application, The Book and Paper Group Annual, vol. Three, 1984, 62 pgs.
Burner, U. et al., "Transient-state and steady-state kinetics of the oxidation of aliphatic and aromatic thiols by horseradish peroxidase," FEBS Letters (1997) 411(2-3):269-274.

(56) References Cited

OTHER PUBLICATIONS

Carey, F.A. et al., Advanced Organic Chemistry Part A: Structure and Mechanisms, Plenum Press, New York and London, pp. 475-479 (1990).
Cayman Chemical, Stearic Acid, obtained online at: https://www.caymanchem.com/pdfs/10011298.pdf, p. 1. (Year: 2017).
Chen, H. et al., "A dual-targeting nanocarrier based on modified chitosan micelles for tumor imaging and therapy," Polym. Chem. 2014, 5, 4734-4746.
Chen, L. et al., "Synthesis and pH sensitivity of carboxymethyl chitosan-based polyampholyte hydrogel for protein carrier matrices," Biomaterials (2004) 25:3725-3732.
Cherrick, G. R. et al., "Indocyanine Green: Observations on Its Physical Properties, Plasma Decay, and Hepatic Extraction," J.Clinical Investigation, 1960, 39, 592-600.
Choi, K. Y. et al., "Self-assembled hyaluronic acid nanoparticles for active tumor targeting," Biomaterials 2010, 31 (1), 106-114.
Chu et al., "Electro-Spinning and Electro-Blowing of Hyaluronic Acid," 2004, Biomacromolecules, vol. 5, pp. 1428-1436. (Year: 2004).
Contipro, Specialty Hyaluronan Chemicals Product Catalog, 52 pgs. (retrieved on Sep. 26, 2018). (Year: 2018).
Cornwell, M.J. et al., "A One-Step Synthesis of Cyclodextrin Monoaldehydes," Tetrahedron Letters (1995) 36(46):8371-8374.
Crescenzi, V. et al., "Novel Hydrogels via Click Chemistry: Synthesis and Potential Biomedical Applications," Biomacromolecules (2007) 8:1844-1850.
Cumpstey, I., Review Article "Chemical Modification of Polysaccharides," ISRN Organic Chemistry (2013) Article ID 417672, 27 pgs.
Czech Official Action in Czech Patent Application No. PV 2009-835, dated Aug. 2010, 2 pgs.
Czech Search Report in Czech Patent Application No. PV 2010-1001, dated Sep. 27, 2011, 1 pg.
Czech Search Report in Czech Patent Application No. PV 2011-241, dated Nov. 30, 2011, 1 pg.
Czech Search Report in Czech Patent Application No. PV 2012-136, dated Sep. 18, 2012, 3 pgs.
Czech Search Report in Czech Patent Application No. PV 2012-282, dated Jan. 30, 2013, 1 pg.
Czech Search Report in Czech Patent Application No. PV 2012-306, dated Feb. 11, 2013, 1 pg.
Czech Search Report in Czech Patent Application No. PV 2012-664, dated May 24, 2013, 3 pgs.
Czech Search Report in Czech Patent Application No. PV 2012-842, dated Aug. 19, 2013, 3 pgs.
Czech Search Report in Czech Patent Application No. PV 2012-843, dated Aug. 20, 2013, 1 pg.
D'Este, M. et al., "A systematic analysis of DMTMM vs EDC/NHS for ligation of amines to Hyaluronan in water," Carbohydr. Polym. 2014, 108, 239-246.
Darr, A. et al., "Synthesis and characterization of tyramine-based hyaluronan hydrogels," Journal of Materials Science: Materials in Medicine (2009) 20(1), 33-44.
Darr, A.; Calabro, A., Synthesis and characterization of tyramine-based hyaluronan hydrogels. Journal of Materials Science: Materials in Medicine 2009, 20 (1), 33-44.

METHOD OF CROSSLINKING OF POLYSACCHARIDES USING PHOTOREMOVABLE PROTECTING GROUPS

FIELD OF INVENTION

The invention relates to polysaccharide crosslinking using photoremovable protecting groups.

BACKGROUND OF THE INVENTION

Hydrogels represent physically or chemically crosslinked polymer structures which are able to absorb large amounts of water without their dissolution in the aqueous solution. Regarding the suitable rheological parameters, the hydrogels with their properties resemble living tissues. Hydrogels are used in form of scaffolds in replacements, or tissues regeneration in case of a tissue damage. The cell organization, cell proliferation or morphogenesis determination may be controlled through hydrogels. At the same time, the hydrogels represent a suitable energy source for the cells. These insoluble three dimensional nets enable the immobilization of biologically active agents (amino acids, peptides, drugs, enzymes, grow factors etc.) and their following controlled release in the desired concentration, time and space. Out of building components of hydrogels, biopolymers are preferred to synthetic polymers, especially where the final application aims at the area of tissue engineering or regenerative medicine and a high biocompatibility of the tested material has to be ensured (Slaughter V. B., Khurshid S. S., Fisher O. Z., Khademhosseini, Peppas, N. A. 2009. *Adv Mater* 21: 3307). Polysaccharides are suitable polymers thanks to their easy availability, a relatively low price, excellent biocompatibility, useful mechanical properties and a manifold structural or functional variability. The most often used polysaccharides for pharmaceutical and biomedical applications are:

Hyaluronic acid (HA) is a natural heteropolysaccharide of glycosaminoglycan kind, formed with D-glucuronic and N-acetyl-D-glucosamine subunit, mutually bound through $\beta(1-3)$ and $\beta(1-4)$ O-glycosidic bond. HA naturally appears in many connective tissues, synovial fluid, aqueous humour, skin and cartilages (Smeds K. A., Pfister-Serres A., Mild G., Dastqheib K., Inoue M., Hatchell D. L., Grinstaff M. W. 2001. *J Biomed Mater Res* 54: 115). Thanks to its biocompatibility, HA is utilized in biomedicine, nutrition, cosmetic and pharmaceutical industry.

Chondroitin sulfate (CS) is a glycosaminoglycan composed of sulfated N-acetylgalactosamine and D-glucuronic acid that is in the greatest amount present in the extracellular matrix of cartilage. CS participates in the articular metabolism and is used as a therapeutic means against degenerative arthritis. As food supplements (e. g. Hyalgel) it plays an important role in prevention of osteoarthrosis (Bottegoni C., Muzzarelli R. A. A., Giovannini F., Busilacchi A., Gigante A. 2014: *CarbPol* 109: 126).

Chitosan (CH) is a cationic homopolysaccharide prepared by deacetylation of chitin and is extracted from exoskeleton of sea crustaceans. As CH comes from a natural, renewable nontoxic and biodegradable source, it is regarded as an ecologically acceptable product. Its quality and properties are dependent on its purity and the degree of deacetylation (usually in the range 70-95%), further on the molecular weight and also on the crystallinity. CH is usually used as a hypocholesterolemic and bacteriostatic preparation, drug vehicle or material for cell scaffold formation (Pasqui D., De Cagna M., Barbucci, R. 2012. *Polymers* 4: 1517). Sodium carboxymethyl cellulose (CMCNa) is a hydrophilic cellulose derivative produced by alkylation of swollen cellulose (homopolymer of $\beta$-D-glucopyranose) with chloroacetic acid under basic conditions. CMCNa, in combination with various drugs or optionally co-excipients, in the form of medical devices (gauze, bandage, wound dressings) is used in the therapy of skin diseases. It is applied in treating of diabetic foot, skin ulcers, post-operative surgery wound, in toxic epidermal necrolysis and also as skin implants (Pasqui D., De Cagna M., Barbucci, R. 2012. *Polymers* 4: 1517).

Polysaccharides in their native form do not form hydrogels. For this reason, an additional modification of their physical properties is required. It is mainly the decrease of solubility and increase of stability in aqueous solution. One option is a chemical modification, through which the polarity of the polysaccharide chain is decreased e. g. by blocking of the carboxyl group resulting in ester formation (U.S. Pat. Nos. 4,851,521, 4,965,353) or by hydrophobization of the polar hydroxyl groups (WO1996/035720, WO2010/105582, U.S. Pat. No. 3,720,662).

The second option is a chemical crosslinking within the polysaccharide structure. The most used reactions leading to a chemical crosslinking include polymerization (Burdick J. A., Chung c., Jia X., Randolph M. A., Langer R. 2005. *Biomacromolecules* 6: 386), condensation reactions (WO2008014787, WO2009/108100, WO2011/069474), dimerization reactions (EP0554898B1, EP0763754A2, US006025444), cycloaddition reactions (CZ304072), optionally enzymatic reactions (CZ303879). Oxidative reactions of polysaccharides according to WO2011/069474 and WO2011/069475 may be used for the synthesis of polysaccharide precursors that are suitable for additional chemical modifications including crosslinking reactions. Dehydration reaction of these precursors was thus used for the preparation of $\alpha,\beta$-unsaturated analogues (CZ304512). Deacetylation of polysaccharides according to U.S. Pat. No. 7,345,117 is used for the preparation of polyamino derivatives required e. g. for nucleophilic addition.

However, classical chemical crosslinking also has several important and indisputable drawbacks, i. e. uncontrollable propagation of chemical reaction, insufficient chemoselectivity, using of crosslinking agents and the necessity of an additional purification of the final products. The combination of the classical chemical polysaccharide crosslinking with the use of photoreactive linkers can successfully overcome the above limitations. The photoreactive linkers contain photoremovable protecting groups (PPG) built in their structure. The preparation of monofunctional photoremovable carbamate linkers can be carried out according to (Figueiredo R. M., Fröhlich R., Christmann M. 2006 *J OrgChem* 71: 4147) or (Werner T., Barrett A. G. M. 2006 *J OrgChem* 71:4302 or Furuta, T., Hirayma Y., Iwamura M. 2001. *OrgLett* 3: 1809) by a reaction of an excess of a bifunctional aminolinker with an acylation agent carrying PPG.

One example of the application of PPG is substrate masking from recognition in biological system in vitro or in vivo, the so-called triggering of the biological response to the presence of a specific agent. These masked substrates are called caged molecules and in case of the used PPG, the term caging groups (CG) is used. CG help mainly in biotechnology and cellular biology as their photocleavage takes place under mild conditions, rapidly, precisely and can be excellently controlled in time and space. The CG applications fall in the area of photolithographic creation of complex peptides, oligonucleotides or in the area of biologically active compounds release in cells or tissues (US2002/0016472).

Another practical example of PPG can be a chemical reaction of two involved functional groups that does not proceed as long as one of them is masked with a photoremovable protecting group (PPG). After the PPG removal, the original reactive group is restored and it reacts with the other participating group in the reaction mixture. The advantage of the two-step process, the installation and cleavage of PPG, thus enables the control of the chemical reaction course. If the substrate in the reaction mixture is masked (protected), the chemical reaction does not proceed. If the substrate is regenerated (released) in the reaction mixture, the chemical reaction proceeds. The amount or the concentration of the masked and released substrate can be determined by using the source of electromagnetic radiation, both in the time aspect (on-off switch, light impulse), and in the space aspect (focused light, laser, use of a pbotomask etc.). Another advantage of the photocleavage is that it can be reliably applied where other approaches of introduction of protecting groups fail. It applies for example for pH-sensitive or thermosensitive substrates, biomaterials and in in vitro or in vivo applications. The approach disclosed here thus enables to control the qualitative parameters (crosslink accuracy and density), as well as the quantity parameters (the whole volume vs part of the sample) of the crosslinked material. For this reason the final crosslinked product can reach from viscous solutions, through soft, to elastic gels.

The term photochemically controlled chemical reaction can represent not only a conjugation reaction or a reaction leading to immobilization or, in the contrary, to the release of the substrate from the carrier structure. This approach can also be applied to the formation of crosslinked polymer structures through the crosslinking reaction with the masked substrate, which is the subject matter of this patent document.

In the literature, there are more practical examples of PPGs that undergo photolysis (Green T. W. & Wuts P. G. M., 1999, John Wiley, 3$^{rd}$ edition). Photolysis (chemical cleavage) of chemical bonds in these groups is the result of the light quantum—photon absorption by the substrate molecule. Photochemical cleavage of the protecting group can be accomplished by a direct chromophore excitation after the absorption of a single photon with the desired energy or by a multiphoton absorption followed by an electron transfer to the protection group (US210/0207078). In case of ammines, the introduced protecting groups are carbamate functional groups. The most used PPGs are alkoxy, or alternatively nitro derivatives of aromatic alcohols (Klán P., Šolomek T., Bochet Ch. G., Blanc A, Givens R., Rubina M., Popik V., Kostikov A., Wirz J. 2013: *ChemRev* 113: 119; US2008/0009630, and also heteroaromatics of coumarin, quinoline, xanthan or thioxanthone type (US2002/0016472). The application of carbamate PPGs falls mainly in the area of combinatorial peptide synthesis or nucleic acids synthesis (Piggot A. M. & Karuzo P. 2005. *Tetr Lett* 46: 8241). Some more patent documents exist (US2013309706A1, US20008028630A1, US20060216324A1), that use photolysis for the surface modification of polymer materials, controlled release of a biologically active compound controlled or, in the contrary, its covalent immobilization to the polymer structure. However, the use of PPGs for the controlled polysaccharide crosslinking has not been published yet. Presumably, the reason is a combination of multiple factors including for example an insufficient molar absorption coefficient of the chosen PPG for the desired wavelength range, a low quantum yield of the photolysis, a slow substrate release, a low stability and hydrophobic character of the PPG, a formation of potentially toxic and absorbing disintegrative photolysis products, their consecutive competitive reaction with the released substrate or the biological material.

SUMMARY OF THE INVENTION

The present invention provides a method for performing crosslinking reactions in polysaccharide solutions that is based on the photochemical control of chemical crosslinking process with the use of carbamate PPG. The term photochemical control represents the photochemical cleavage of the carbamate bond (—NH—CO—O—) forming the respective amino group (—HN$_2$) using the electromagnetic radiation. The term chemically crosslinking process represents a condensation reaction of the released amino group with an aldehyde group forming an imino group (—N=CH—). Both simultaneously running processes can be performed under physiologically acceptable conditions.

The advantage of the suggested solution in comparison to methods of polysaccharide crosslinking used up to now is the temporal and spatial control over the course of crosslinking, which enables the preparation of advanced materials for tissue engineering where it is possible to influence the crosslink density and thus also the mechanic properties in the material structures. The photochemical control is very advantageous in the cases when it is desirable to regulate the cell growth in a given environment, which is essential e. g. for biomaterials designated for the reparation of neural tissues (Perale G. et. al 2011. *ACS Chem. Neursci.* 2: 336) or in the production of injectable hydrogels in an effort to minimize the impact of classical invasive surgery (Pasqui D., De Cagna M., Barbucci R. 2012. *Polymers* 4: 1517).

With the combination of the classical chemical crosslinking with the photoreactive polysaccharide derivatives it is possible to achieve the advantages of temporal control of crosslinking reaction progress in such a way that the reaction proceeds only when the respective material is irradiated with the electromagnetic radiation. Under normal conditions, the crosslinking reaction proceeds until running out of the starting material, which is undesired in the cases when specific properties of the crosslinked product are desired, such as material tenacity, pore size, permeability or biodegradability. Also the spatial control over the reaction progress in the form of a proper photomask or focused light ensures local proceeding of the crosslinking reaction in the reaction mixture. A typical example is the photolitographic approach of hydrogel forming, which uses the light for the transfer of a geometrical photomask pattern to a light sensitive substrate (Khetan S., Burdick J. A. (2010). *Biomaterials*, 31: 8228).

Another advantage of the PPG introduction in the polysaccharide structure is the chemospecific course of photolysis and secondly also the crosslinking reaction. The light of desired energy excites only those PPGs which photolytically generate reactive sites for the following crosslinking reaction in exactly defined sites in the polysaccharide polymer structure. Further, the photolysis and the crosslinking reactions proceed under physiological conditions without the requirement of an additional crosslinking agent, organic solvent or isolation of the final crosslinked products that form gels in an aqueous environment, have an enhanced hydrolytic stability, show sorption properties and ensure retention of liquids and the present agents. The application of these crosslinked polysaccharides belong to the area of tissue engineering, regenerative medicine or biomedical applications in the form of scaffolds, implants or drug carriers.

The carbamate derivatives of polysaccharides according to the present invention are understood to be derivatives that possess a carbamate PPG built in their structure either directly or via a proper linker derived from diamine, amino alcohol, dihydrazide, amino acid, alkoxyamine, eventually via a linker with a combination of the following groups: —OH, —NH$_2$, —O—NH$_2$, —COOH, —CONHNH$_2$, —NH—NH$_2$, —SH.

It is further defined that the carbamate PPG group is derived from an aromatic or heteroaromatic alcohol that shows absorption of electromagnetic radiation within the range 320-400 nm, preferably 330-370 nm.

The carbamate PPG is photolysed (cleaved photochemically) during the radiation with electromagnetic light to an aromatic alcohol, carbon dioxide and a compound with the released amine or hydrazide group. This amine or hydrazide group interacts with an aldehyde group of the other (unsubstituted) polysaccharide forming an imine or hydrazone group. Both the first and the second polysaccharide (polysaccharide 1 and polysaccharide 2) can be of identical or different structure of the hyaluronan, chondroitin sulfate or cellulose type, eventually pharmaceutically acceptable derivatives and/or salts thereof. The crosslinking among the polysaccharide derivatives occurs through condensation reactions. The carbamate PPG photolysis demands the presence of water and it proceeds based on and only after the material irradiation with electromagnetic radiation. The photolysis further proceeds simultaneously with the crosslinking reaction and can be performed under physiological conditions or in the presence of other additives (organic, inorganic salts or buffers).

The present invention therefore discloses a method of crosslinking reaction realization in aqueous polysaccharide solutions that is controlled photochemically. Due to the photochemical control the presence of carbamate photoremovable group (PPG) is necessary, as the carbamate group protects the amino group (—NH$_2$) of the polysaccharide derivative from an early or undesirable reaction with the aldehyde group of the other polysaccharide that is present in the reaction mixture. If the amino group is not protected, an uncontrollable reaction occurs without any way to influence the course thereof.

If the protecting PPG group is present, the reaction between the amino group and the aldehyde group occurs in the aqueous reaction mixture only when the reaction mixture is subjected to the electromagnetic radiation, preferably UVA within the range of wavelengths from 320 to 400 nm. This enables the temporal control of the reaction, for example with the radiation source switch, or shading of the reaction mixture. The crosslinking density grows with the increasing radiation time, see FIG. 1, Examples 8 and 9. The spatial control of the reaction for example with a photomask or a light beam occurs only in the irradiated places, see FIG. 2.

The present invention particularly relates to a method of preparation of crosslinked polysaccharide materials according to the general formula (I)

polysaccharide1-R$^1$—N=CH-polysaccharide2      (I), where polysaccharide1 and polysaccharide2 are identical or different polysaccharides and R$^1$ is C$_1$-C$_{30}$ alkyl residue, C$_1$-C$_{30}$ alkylaryl residue or C$_1$-C$_{30}$ alkylheteroaryl residue, optionally containing one or more identical or different heteroatoms selected from the group comprising N, O, S. The method is performed in the following way: an aqueous solution of the aldehyde of polysaccharide2 according to the general formula III polysaccharide2-CH=O      (III), where the substitution degree of aldehyde in polysaccharide2 is within the range of 1 to 50%, is added to an aqueous solution of polysaccharide1 substituted with amine group modified by a photoremovable group according to the general formula (II)

polysaccharide1-R$^1$—NH—CO—O—CH$_2$—R$^2$      (II), where R$^1$ is defined above; R$^2$ is an aromatic system and where the substitution degree of carbamate is within the range of 1 to 10%.

The reaction mixture is subjected to an electromagnetic radiation and at the same time deoxygenation takes place of the mixture.

The reaction can be expressed with the general scheme 1:

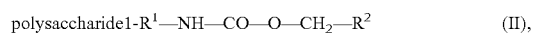

Scheme 1

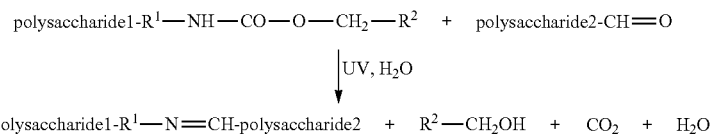

polysaccharide1-R$^1$—NH—CO—O—CH$_2$—R$^2$   +   polysaccharide2-CH=O

↓ UV, H$_2$O polysaccharide1-R$^1$—N=CH-polysaccharide2   +   R$^2$—CH$_2$OH   +   CO$_2$   +   H$_2$O Scheme 1 actually includes two simultaneously proceeding reactions, the photolysis of PPG in polysaccharide 1 and the condensation/crosslinking reaction of the amine of polysaccharide 1 with the aldehyde of polysaccharide 2:

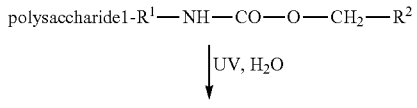

Scheme 1a-Photolysis polysaccharide1-R$^1$—NH—CO—O—CH$_2$—R$^2$

↓ UV, H$_2$O polysaccharide1-R$^1$—NH$_2$   +   R$^2$—CH$_2$OH   +   CO$_2$

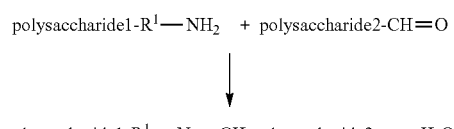

Scheme1b-Crosslinking polysaccharide1-R$^1$—NH$_2$   +   polysaccharide2-CH=O

↓ polysaccharide1-R$^1$—N=CH-polysaccharide2   +   H$_2$O

The nitrogen or NH group in the formulae (I) and (II) is indicated in addition, although it is a part of the group $R^1$. Also the group CH in the formula (I) or CH=O in the formula (III) is indicated in addition, although it is a part of polysaccharide2. Those skilled in the art will understand that it is done only for a better understanding and lucidity of the reaction and the reaction substrates.

As presented above, the degree of substitution of PPG in polysaccharide 1 is within the range of 1 to 10%, preferably 3 to 10%, and its molecular weight is 10 to 400 kDa, preferably 20 to 300 kDa, more preferably 20 to 100 kDa. The degree of polysaccharide2 substitution to an aldehyde is within the range of 1 to 50%, preferably 3 to 25% and its molecular weight is 10 to 800 kDa, preferably 50 to 250 kDa. The preferred polysaccharides include for example hyaluronan, chondroitin sulfate, cellulose and pharmaceutically acceptable derivatives and/or salts thereof.

$R^1$ is preferably selected from a group comprising dihydrazide adipate and hexamethylenediamine and $R^2$ is preferably a condensed aromatic system, more preferably selected from a group comprising pyrene, anthracene, phenanthrene, perylene, anthraquinone, coumarin and substitution derivatives thereof, that may contain atoms C, H, O, S, N in their structure and show absorption of electromagnetic radiation, most preferably $R^2$ is pyrene.

The weight ratio of polysaccharide 1 to polysaccharide 2 is preferably within the range 1:2 to 2:1. Aqueous solutions of polysaccharides 1 and 2 may further contain water soluble agents selected from a group comprising inorganic salts or buffers, preferably phosphate buffer, whereas pH of the solution is within the range of 6.5 to 7.5, preferably 7.0.

The reaction mixture prepared by the method described in the present invention is subjected to the electromagnetic radiation for 0.25 to 2 hours, preferably 0.5 to 1 hour, at the temperature of 10 to 50° C., preferably 20 to 35° C., whereas the electromagnetic radiation used has the wavelength within the range of 320-400 nm, preferably 330-370 nm. As was stated above, the advantage of the invention is that the reaction can be temporal controlled using an electromagnetic radiation source switch or a pulse source of electromagnetic radiation or shading of the reaction mixture. The present invention further also allows the spatial control of the reaction using a photomask, the focused electromagnetic radiation or a beam of electromagnetic radiation.

The material produced according to the present invention can be used in the field of tissue engineering or regenerative medicine in the form of scaffolds, fillers or in the field of biomedicine in the form of drug carriers based on photosensitive materials with the controlled release of the biologically active agent.

DETAILED DESCRIPTION OF DRAWINGS

FIG. 1 represents the use of upside-down method for determination of gelation in the reaction mixture. (a) Solution of two-component reaction mixture (Pmoc-DHA-HA and HA-aldehyde) before photolysis. (b) Hydrogel of the crosslinked product (HA-DHA-HA) after photolysis. (c) Hydrogel of crosslinked product (HA-DHA-HA) after 1 h in PBS (pH=7.4, c=0.9%, w/v).

Figure 2:
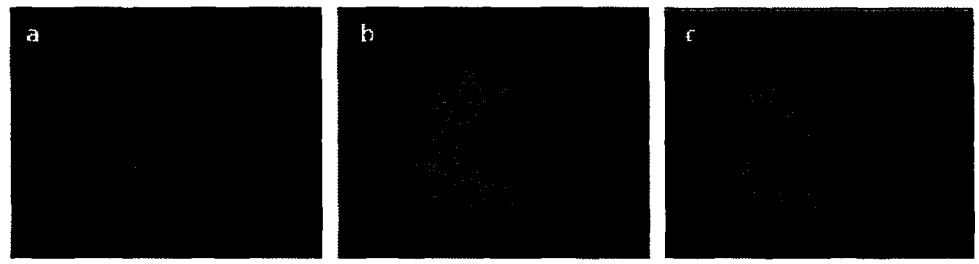

FIG. 2 illustrates the spatial control of the crosslinking reaction (Pmoc-DHA-HA and HA-aldehyde) using a photomask in the shape of a semi-circle on 50% of the surface of the reaction mixture. (a) the reaction mixture after photolysis, (b) the reaction mixture after 15 min in PBS (pH=7.4, c=0.9% w/v) and decanting of PBS solution, (c) the reaction mixture after 15 min in PBS (pH=7.4, c=0.9% w/v) and adding new portion of PBS.

Figure 3:
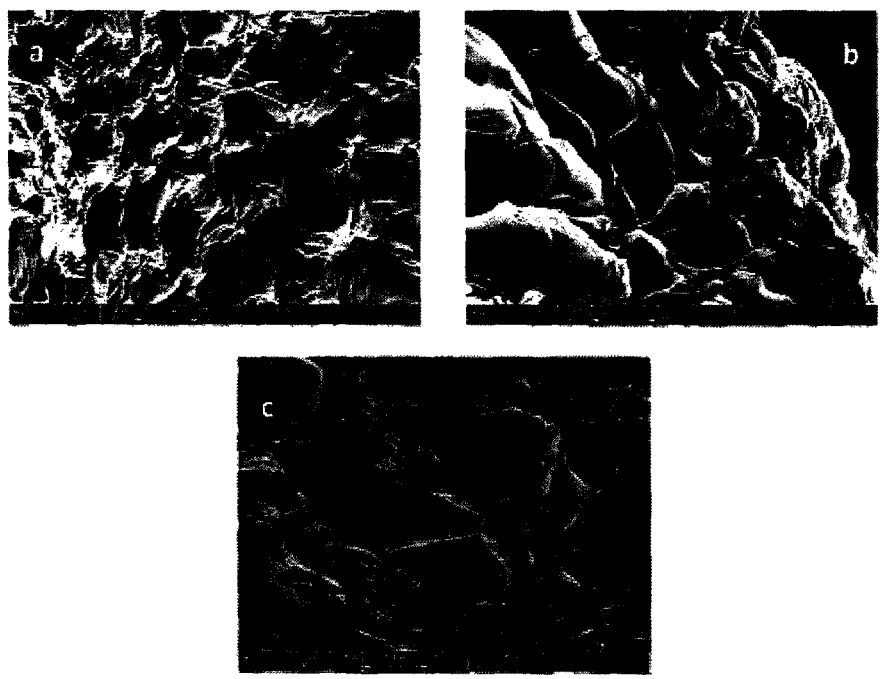

FIG. 3 shows microscopic photographs of freeze-dried samples. (a): the hydrogel surface (100×), (b) the cross-section of the hydrogel (100×), (c) the cross-section of the hydrogel after 1 h in PBS (pH=7.4, c=0.9% w/v).

EXAMPLES

The term equivalent (eqv) used herein relates to a disaccharide of hyaluronic acid, disaccharide of chondroitin sulfate or monosaccharide of sodium carboxymethyl cellulose, if not stated otherwise. Percentage is used as mass percentage, if not stated otherwise.

The molecular weight of the initial hyaluronic acid (source: Contipro Pharma a.s., Dolní Dobrouč, CZ) is the average molecular weight within the range of $10^4$ to $10^6$ g·mol$^{-1}$ and was determined by SEC-MALLS.

The molecular weight of the initial chondroitin sulfate (source: Sigma-Aldrich s.r.o., Prague, CZ) is the average molecular weight within the range of $4 \times 10^4$ to $5 \times 10^4$ Da or g·mol$^{-1}$ and was determined with the method SEC-MALLS. The ratio of chondroitin-4-sulfate (C4S) and chondroitin-6-sulfate (C6S) was 2:3. The material was isolated from an animal material.

The molecular weight of the initial sodium carboxymethyl cellulose (source: Sigma-Aldrich s.r.o., Prague, CZ) is the average molecular weight within the range of $22 \times 10^4$ to $25 \times 10^4$ g·mol$^{-1}$ and was determined with SEC-MALLS. The degree of alkylation with the carboxymethyl group was 70%.

The degree of substitution or modification in the structure of glycosaminoglycans was determined by means of the following calculation:

DS=substitution degree=100%*(the molar amount of the bound substituent or modified disaccharide)/(the molar amount of all disaccharides)

The degree of modification in the structure of sodium carboxymethyl cellulose was determined by means of the following calculation:

DS=substitution degree=100%*(the molar amount of the bound substituent or modified monosaccharide)/(the molar amount of all monosaccharides)

PPG=photoremovable protection group
DHA=dihydrazide adipate
HMD=1,6-hexamethylenediamine
Pmoc=pyren-1-ylmethoxycarbonyl
UVA=near ultraviolet radiation within the range of wavelengths 320-400 nm, emitted by longwave ultraviolet source Black-Ray mercury spot lamp, model B-100A (UVP) with declared λmax=365 nm.

The surface morphology of the freeze-dried gels was analyzed with scanning electron microscope Zeiss Ultra Plus.

Deacetylated hyaluronic acid was prepared by deacetylation with hydrazine according to Buffa R., et al. in CZ304512.

Oxidation of polysaccharides was performed according to Buffa R, et al.: WO2011069474 and WO2011069475.

Example 1. Preparation of Pmoc-Dihydrazide Adipate Hyaluronan (Pmoc-DHA-HA)

HA aldehyde (100 mg, 0.265 mmol, DS=43%, Mw=1.35× $10^5$ g/mol) was dissolved in 5 mL of distilled water (solution I). Pmoc-DHA (54 mg, 0.126 mmol) was dissolved in 5 mL of DMSO (solution II). Both solutions were mixed and reacted for 24 h at room temperature. In the second step PicBH₃ (81 mg, 0.754 mmol) was added. The reaction mixture was stirred for 48 h at room temperature. The product was precipitated with IPA.

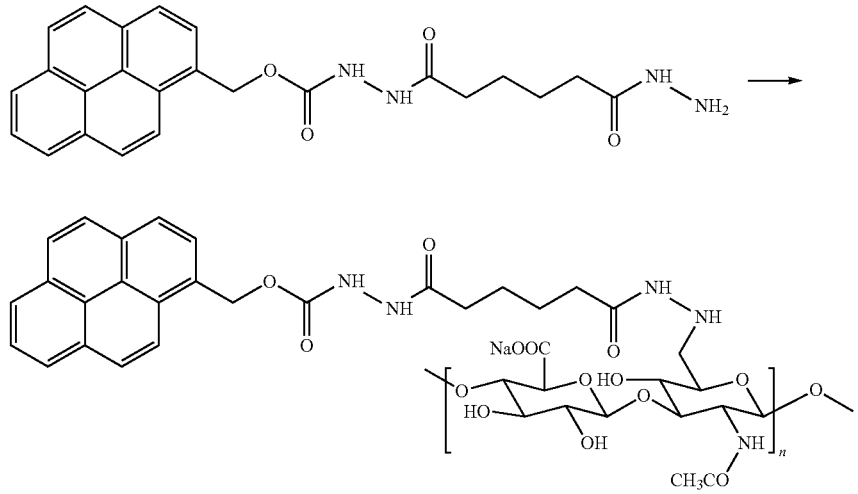

DS=10%, Mw=0.34×10⁵ g/mol, isolated yield 85%

| | |
|---|---|
| ¹H NMR (D₂O) | δ 1.60 (bs, 4H); 2.21 (bs, 2H); 2.25 (bs, 2H); 2.98 (bs, 1H, polymer-N$_{6a}$); 3.26 (bs, 1H, polymer-N$_{6b}$); 5.89 (s, 2H, —CH₂-pyr); 7.98-8.41 (m, 9H$_{Ar}$) ppm |
| H-H COSY (D₂O) cross-peak | δ 1.60-2.21; 1.60-2.25; 2.98-3.26 ppm |
| HSQC (D₂O) cross-peak | δ 1.60 (¹H)-24.6 (¹³C); 2.21 (¹H)-33.0 (¹³C); 2.25 (¹H)-33.0 (¹³C); 2.98 (¹H)-50.0 (¹³C); 3.26 (¹H)-50.0 (¹³C); 5.89 (¹H)-64.3 (¹³C); 7.98 (¹H)-124.2 (¹³C); 8.05 (¹H)-125.3 (¹³C); 8.30 (¹H)-129.6 (¹³C); 8.41 (¹H)-131.2 (¹³C) ppm |
| DOSY NMR (D₂O) | log D (1.60 ppm, 2x-CH₂-linker)~−10.70 m²/s<br>log D (2.03 ppm, Me—CO—NH-polymer)~−10.70 m²/s<br>log D (2.21 ppm, —CH₂—CONHNH₂)~−10.70 m²/s<br>log D (2.25 ppm, —CH₂—CONHNH-polymer)~−10.70 m²/s<br>log D (2.98 ppm, polymer-N$_{6a}$)~−10.70 m²/s<br>log D (3.26 ppm, polymer-N$_{6b}$)~−10.70 m²/s<br>log D (5.89 ppm, —CH₂-pyr)~−10.70 m²/s<br>log D (7.98-8.41 ppm, —CH₂-pyr)~−10.70 m²/s<br>log D (4.72 ppm, H₂O)~−8.6 m²/s |
| UV/Vis (0.01%, H₂O) | λ$_{max1,2}$ = 350, 329 nm |

Example 2. Preparation of Pmoc-Hexamethylene Diamine Hyaluronan (Pmoc-HMD-HA)

HA aldehyde (100 mg, 0.265 mmol, DS=10%, Mw=1.92×10⁵ g/mol) was dissolved in 5 mL of distilled water (solution I). Pmoc-HMD (19 mg, 0.05 mmol) was dissolved in 5 mL of DMSO (solution II). Both solutions were mixed and reacted for 24 h at room temperature. In the second step PicBH₃ (81 mg, 0.754 mmol) was added. The reaction mixture was stirred for 48 hours at room temperature. The product was obtained by precipitation with IPA.

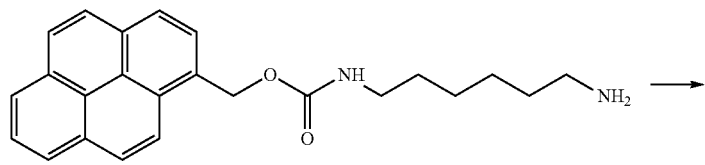

-continued

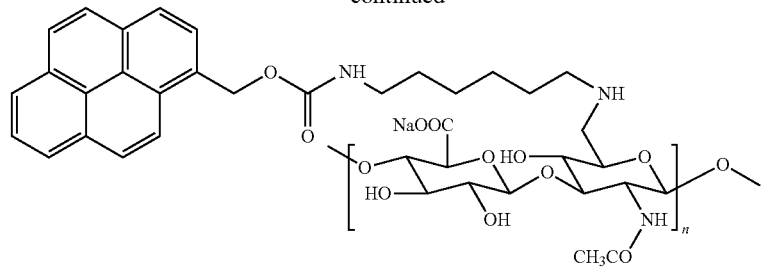

DS=7%, Mw=1.92×10⁵ g/mol, isolated yield 71%.

| | |
|---|---|
| $^1$H NMR (D$_2$O) | δ 1.34 (bs, 4H); 1.45 (bs, 2H); 1.66 (bs; 2H; 2H); 3.05 (bs; 2H; —CH$_2$—NHCO-pyr); 3.15 (bs; 2H; —CH$_2$—NH-polymer); 3.26 (bs; 1H; polymer-N$_{6a}$); 3.48 (bs; 1H; polymer-N$_{6b}$); 5.83 (bs, 2H, —CH$_2$-pyr), 8.00-8.45 (m, 9H$_{Ar}$) ppm |
| H-H COSY (D$_2$O) cross-peak | δ 1.34-1.45; 1.34-1.66; 1.66-3.05; 1.45-3.15; 3.26-3.48 ppm |
| HSQC (D$_2$O) cross-peak | δ 1.34 ($^1$H)-26.3 ($^{13}$C); 1.45 ($^1$H)-28.7 ($^{13}$C); 1.66 ($^1$H)-26.1 ($^{13}$C); 3.05 ($^1$H)-48.2 ($^{13}$C); 3.15 ($^1$H)-41.3 ($^{13}$C); 3.26 ($^1$H)-48.5 ($^{13}$C); 3.48 ($^1$H)-48.5 ($^{13}$C); 5.83 ($^1$H)-64.3 ($^{13}$C); 8.00 ($^1$H)-124.2 ($^{13}$C); 8.09 ($^1$H)-125.7 ($^{13}$C); 8.26 ($^1$H)-130.1 ($^{13}$C); 8.45 ($^1$H)-131.7 ($^{13}$C) ppm |
| DOSY NMR (D$_2$O) | log D (1.34 ppm, 2x-CH$_2$-linker)~−10.60 m$^2$/s<br>log D (1.45 ppm, —CH$_2$-linker)~−10.60 m$^2$/s<br>log D (1.66 ppm, —CH$_2$-linker)~−10.60 m$^2$/s<br>log D (2.03 ppm, Me—CO—NH-polymer)~−10.60 m$^2$/s<br>log D (3.05 ppm, —CH$_2$—NHCO—)~−10.60 m$^2$/s<br>log D (3.15 ppm, —CH$_2$—NH-polymer)~−10.60 m$^2$/s<br>log D (3.26 ppm, polymer-N$_{6a}$)~−10.60 m$^2$/s<br>log D (3.48 ppm, polymer-N$_{6b}$)~−10.60 m$^2$/s<br>log D (5.83 ppm, —CH$_2$-pyr)~−10.60 m$^2$/s<br>log D (8.00-8.45 ppm, H$_{Ar}$)~−10.60 m$^2$/s<br>log D (4.72 ppm, H$_2$O)~−8.6 m$^2$/s |
| UV/Vis (0.01%, H$_2$O) | λ$_{max1,2}$ = 348, 330 nm |

Example 3. Preparation of Pmoc-Dihydrazide Adipate Chondroitin Sulfate (Pmoc-DHA-CS)

CS aldehyde (50 mg, 0.10 mmol, DS=14%, Mw=3.0-4.0× 10⁵ g/mol) was dissolved in 2.5 mL of distilled water (solution I). Pmoc-DHA (8.7 mg, 0.02 mmol, 0.2 eqv.) was dissolved in 2.5 mL of DMSO (solution II). Both solutions were mixed and reacted for 24 h at room temperature. In the second step PicBH$_3$ (32 mg, 0.3 mmol, 3 eqv.) was added. The reaction mixture was stirred for 48 h at room temperature. The product was obtained with precipitation with IPA.

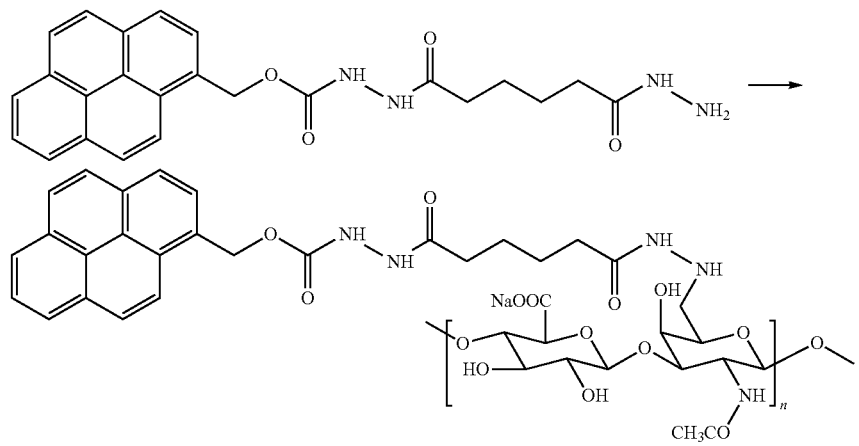

DS=5-6%, Mw=3.0-4.0×10$^5$ g/mol, isolated yield 84%

| | |
|---|---|
| $^1$H NMR (D$_2$O) | δ 1.66 (bs, 4H); 2.25-2.32 (m, 4H); 3.00 (bs, 1H, polymer-N$_{6a}$); 3.25 (bs, 1H, polymer-N$_{6b}$); 5.89 (bs, 2H, —CH$_2$-pyr); 8.15-8.38 (m, 9H$_{Ar}$) ppm |
| H-H COSY (D$_2$O) cross-peak | δ 1.66-2.25; 1.66-2.32; 3.00-3.25 ppm |
| HSQC (D$_2$O) cross-peak | δ 1.66 ($^1$H)-25.0 ($^{13}$C); 2.25 ($^1$H)-31.2 ($^{13}$C); 2.32 ($^1$H)-32.8 ($^{13}$C); 3.00 ($^1$H)-50.6 ($^{13}$C); 3.25 ($^1$H)-50.6 ($^{13}$C); 5.89 ($^1$H)-64.6 ($^{13}$C); 8.16 ($^1$H)-124.8 ($^{13}$C); 8.38 ($^1$H)-125.6 ($^{13}$C); 8.30 ($^1$H)-129.6 ($^{13}$C) ppm |
| DOSY NMR (D$_2$O) | log D (1.66 ppm, 2x-CH$_2$-linker)~−10.50 m$^2$/s<br>log D (2.04 ppm, Me—CO—NH-polymer)~−10.50 m$^2$/s<br>log D (2.25-2.32 ppm, —CH$_2$—CONHNH2, —CH$_2$—CONHNHpolymer)~−10.50 m$^2$/s<br>log D (3.00 ppm, polymer-N$_{6a}$)~−10.50 m$^2$/s<br>log D (3.25 ppm, polymer-N$_{6b}$)~−10.50 m$^2$/s<br>log D (5.89 ppm, —CH$_2$-pyr)~−10.50 m$^2$/s<br>log D (8.15-8.38 ppm, —CH2-pyr)~−10.50 m$^2$/s<br>log D (4.72 ppm, H$_2$O)~−8.6 m$^2$/s |
| UV/Vis (0.01%, H$_2$O) | λ$_{max1,2}$ = 343, 328 nm |

Example 4. Preparation of Pmoc-Dihydrazide Adipate of Sodium Carboxymethyl Cellulose (Pmoc-DHA-CMCNa)

CMCNa aldehyde (100 mg, 0.45 mmol, DS=4-5%, Mw=8.2×10$^5$ g/mol) was dissolved in 5 mL of distilled water (solution I). Pmoc-DHA (19.4 mg, 0.045 mmol, 0.1 eqv.) was dissolved in 5 mL of DMSO (solution II). Both solutions were mixed and reacted for 24 h at room temperature. In the second step PicBH$_3$ (144 mg, 1.345 mmol, 3 eqv.) was added. The reaction mixture was stirred for 48 h at room temperature. The product was obtained by precipitation with IPA.

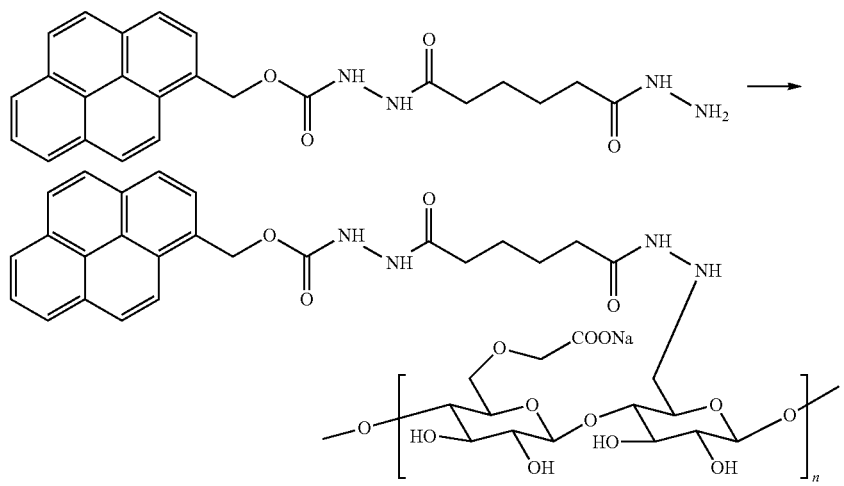

DS=2%, Mw=0.80×10$^5$ g/mol, isolated yield 88%

| | |
|---|---|
| $^1$H NMR (D$_2$O) | δ 1.60-1.65 (bs, 4H); 2.22 (bs, 2H); 2.38 (bs, 2H); 3.00 (bs, 1H, polymer-H$_{6a}$); 3.37 (bs, 1H, polymer-H$_{6b}$); 5.84-5.87 (bs, 2H, —CH$_2$-pyr); 8.05-8.33 (m, 9H$_{Ar}$) ppm |
| H-H COSY (D$_2$O) cross-peak | δ 1.60-2.22; 1.65-2.38; 3.00-3.37 ppm |
| HSQC (D$_2$O) cross-peak | δ 1.60-1.65 ($^1$H)-25.3 ($^{13}$C); 2.22 ($^1$H)-33.6 ($^{13}$C); 2.38 ($^1$H)-32.7 ($^{13}$C); 3.00 ($^1$H)-50.1 ($^{13}$C); 3.37 ($^1$H)-51.3 ($^{13}$C); 5.84-5.87 ($^1$H)-64.2 ($^{13}$C); 8.05 ($^1$H)-123.5 ($^{13}$C); 8.30 ($^1$H)-125.1 ($^{13}$C); 8.33 ($^1$H)-129.4 ($^{13}$C) ppm |
| DOSY NMR (D$_2$O) | log D (1.60-1.65 ppm, 2x-CH$_2$-linker)~−10.60 m$^2$/s<br>log D (2.22-2.38 ppm, —CH$_2$—CONHNH$_2$, —CH$_2$—CONHNHpolymer)~−10.60 m$^2$/s<br>log D (3.00 ppm, polymer-N$_{6a}$)~−10.60 m$^2$/s |

| | |
|---|---|
| | log D (3.37 ppm, polymer-$N_{6b}$)~−10.60 m²/s |
| | log D (4.55-4.61 ppm, H1aH1'-polymer)~−10.60 m2/s |
| | log D (5.84-5.87 ppm, —$CH_2$-pyr)~−10.60 m²/s |
| | log D (8.05-8.33 ppm, =$CH_2$-pyr)~−10.60 m²/s |
| | log D (4.72 ppm, $H_2O$)~−8.6 m²/s |
| FT-IR (KBr) | C=O st 1750-1680 cm⁻¹ (carbamate) |
| | N—CO—O st as 1270-1210 cm⁻¹ (carbamate) |
| | st sy 1050-850 cm⁻¹ (carbamate) |
| UV/Vis (0.01%, $H_2O$) | $\lambda_{max1,2}$ = 344, 329 nm |

Example 5. Preparation of Pmoc-HMD-HA

Pmoc-1-H-imidazole carboxylate (326 mg, 1 mmol) dissolved in 20 mL THF was added to 20 mL of an aqueous solution of HMD-HA (200 mg, 0.5 mmol, DS=36%) and the reaction mixture was stirred for 24 h at room temperature. The product (DS=8%, Y=40%) was obtained by precipitation with IPA.

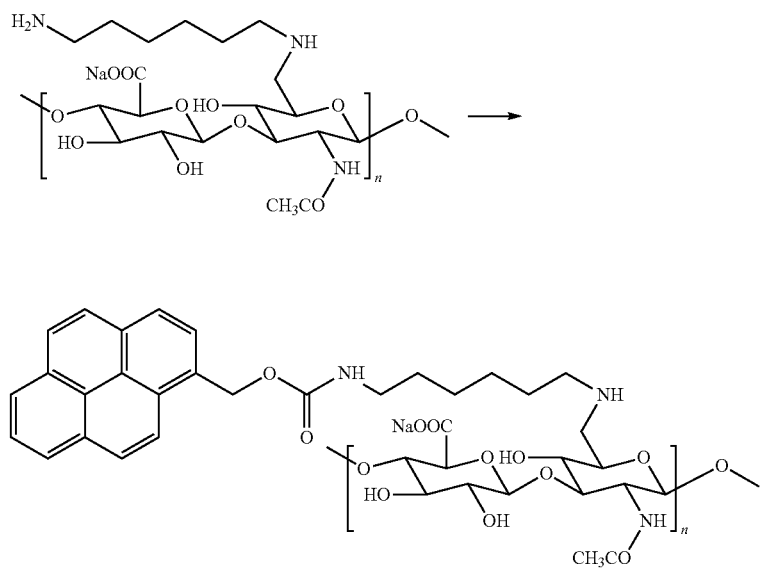

The structural analysis of the product is shown in Example 2.

Example 6. Preparation of Pmoc-DHA-HA

Pmoc-1-H-imidazole carboxylate (326 mg, 1 mmol) dissolved in 20 mL THF was added to 20 mL of an aqueous solution of DHA-HA (200 mg, 0.5 mmol, DS=25%) and the reaction mixture was stirred for 24 h at room temperature. The product (DS=6%, Y=45%) was obtained by precipitation with IPA.

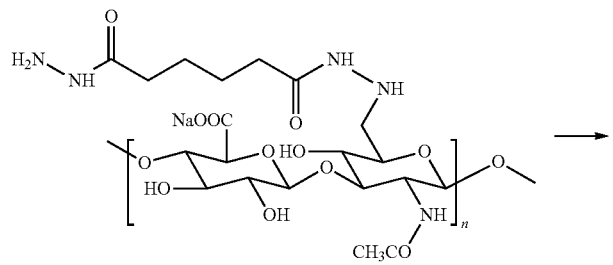

-continued

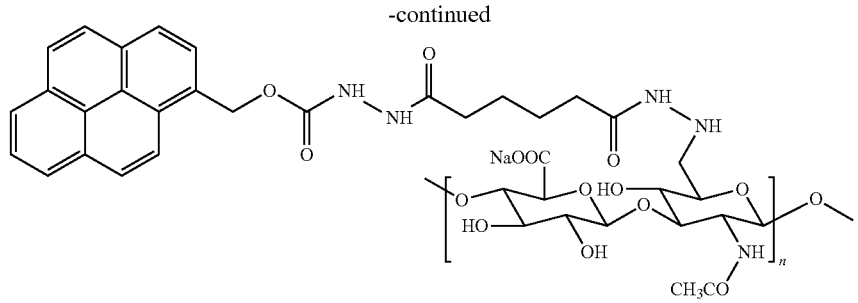

The structural analysis of the product is shown in Example 1.

Example 7. Preparation of Pmoc-Deacetylated Hyaluronan (Pmoc-DEA-HA)

Pmoc-1-H-imidazole carboxylate (326 mg, 1 mmol) dissolved in 20 mL of THF was added to 20 mL of an aqueous solution DEA-HA (200 mg, 0.5 mmol, DS=32%, Mw=0.37× $10^5$ g/mol) and the reaction mixture was stirred for 24 h at 40° C. The product was obtained by precipitation with IPA.

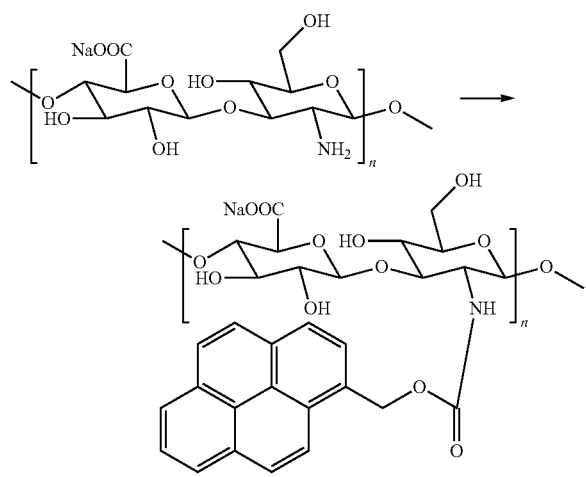

DS=7%, isolated yield 35%

| | |
|---|---|
| $^1$H NMR (D$_2$O) | δ 3.70 (bs, 1H, N2); 5.86 (bs, 2H, —CH$_2$-pyr); 8.10-8.35 (m, 9H, pyr) ppm |
| HSQC (D2O) cross-peak | δ 3.70 ($^1$H)-56.3 ($^{13}$C); 5.86 ($^1$H)-63.90 ($^{13}$C); 8.10 ($^1$H)-124.0 ($^{13}$C); 8.20 ($^1$H)-125.4 ($^{13}$C); 8.30 ($^1$H)-129.0 ($^{13}$C); 8.35 ($^1$H)-131.8 ($^{13}$C) ppm |
| UV/Vis (0.01%, H$_2$O) | $\lambda_{max1,2}$ = 348, 329 nm |

Example 8. Photolysis of Pmoc-DHA-HA in the Presence of HA-Aldehyde and Crosslinking Method 1: Pmoc-DHA-HA (10 mg, 0.025 mmol, DS=10%, Mw=2.64×$10^5$ g/mol) was dissolved in 2 mL of D$_2$O in a quartz flask. HA-aldehyde (10 mg, 0.025 mmol, DS=11%, Mw=0.66×$10^5$ g/mol) was added. The sample was deoxygenated with a stream of nitrogen and was irradiated for 1 h in UVA under N$_2$ at 25° C., pH=7 while stirred, while samples were taken in 15 minute intervals for $^1$H NMR analysis. The increase of the crosslink density (δ=7.49 ppm, HA-CH=N-HA) was monitored at particular time intervals (15/30/45/60 min) at the level (18/31/66/85%), respectively.

Example 9. Photolysis of Pmoc-DHA-HA in the Presence of α,β-Unsaturated HA-Aldehyde and Crosslinking Method 1: Pmoc-DHA-HA (10 mg, 0.025 mmol, DS=10%, Mw=2.64×$10^5$ g/mol) was dissolved in 2 mL of D$_2$O in a quartz flask. α,β-Unsaturated HA-aldehyde (10 mg, 0.025 mmol, DS=5%, Mw=0.68×$10^5$ g/mol) was added. The sample was deoxygenated in the stream of N$_2$ and irradiated for 1 h in UVA under N$_2$ at 25° C., pH=7 while stirred, while samples for $^1$H NMR analysis were taken in 15 minutes intervals. The increase of the crosslink density (δ=7.58 ppm (H6) and 5.60 ppm (H4), HA-CH=N-HA) was monitored at particular time intervals (15/30/45/60 min) at the level (20/32/48/75%), respectively.

Example 10. Photolysis of Pmoc-DHA-HA in the Presence of Saturated HA-Aldehyde and Crosslinking Method 1: Pmoc-DHA-HA (10 mg, 0.025 mmol, DS=10%, Mw=2.64×$10^5$ g/mol) was dissolved in 2 mL D$_2$O in quartz flask. HA-aldehyde (10 mg, 0.025 mmol, DS=11%, Mw=0.66×$10^5$ g/mol) was added. The sample was deoxygenated in the stream of N$_2$ and was irradiated for 1 h in UVA under N$_2$ at 25° C., pH=7 while stirred whereas aliquots for $^1$H NMR analysis were withdrawn in 15 minute intervals. After 60 min UV exposition 85% of hydrazone was formed (δ=7.49 ppm, HA-CH=N-HA).

Method 2: Pmoc-DHA-HA (10 mg, 0.025 mmol, DS=10%, Mw=2.64×$10^5$ g/mol) was dissolved in 2 mL of D$_2$O in a quartz flask. HA-aldehyde (10 mg, 0.025 mmol, DS=45%, Mw=0.35×$10^5$ g/mol) was added. The sample was deoxygenated in the stream of nitrogen and irradiated for 1 h in UVA under N$_2$ at 25° C., pH=7 while stirred, wherein samples for $^1$H HMR analysis were taken in 15 minute intervals. After 60 min of UV exposition, 95% of hydrazone was formed (δ=7.49 ppm, HA-CH=N-HA).

Method 3: Pmoc-DHA-HA (10 mg, 0.025 mmol, DS=10%, Mw=2.64×$10^5$ g/mol) was dissolved in 2 mL of PBS (c=0.9%, pH=7.4) in a quartz flask. HA-aldehyde (10 mg, 0.025 mmol, DS=11%, Mw=5.10×$10^5$ g/mol) was added. The sample was deoxygenated in the stream of nitrogen and irradiated for 1 h in UVA under N$_2$ at 37° C., pH=7 while stirred. After 1 h of UVA exposition, the viscosity of the solution increased.

Method 4: Pmoc-DHA-HA (10 mg, 0.025 mmol, DS=10%, Mw=2.64×$10^5$ g/mol) was dissolved in 2 mL of PBS (c=0.9%, pH=7.4) in a quartz flask. HA-aldehyde (10 mg, 0.025 mmol, DS=11%, Mw=5.1×10⁵ g/mol) was added. The sample was deoxygenated in the stream of nitrogen and was irradiated for 1 h in UVA, under $N_2$ at 50° C., at 25° C., pH=7 while stirred. After 1 h of UVA exposition, the viscosity of the solution increased.

Method 5: Pmoc-DHA-HA (10 mg, 0.025 mmol, DS=10%, Mw=2.64×10⁵ g/mol) was dissolved in 3 mL of PBS (c=0.9%, pH=7.4) in a quartz flask. HA-aldehyde (20 mg, 0.050 mmol, DS=11%, Mw=5.10×10⁵ g/mol) was added. The sample was deoxygenated in the stream of nitrogen and was irradiated for 1 h in UVA, under $N_2$, at 25° C., pH=7 while stirred. After 1 h of UVA exposition, a gel was formed.

Method 6: Pmoc-DHA-HA (10 mg, 0.025 mmol, DS=10%, Mw=2.64×10⁵ g/mol) was dissolved in 3 mL of PBS (c=0.9%, pH=7.4) in a quartz flask. HA-aldehyde (20 mg, 0.050 mmol, DS=11%, Mw=5.10×10⁵ g/mol) was added. The sample was deoxygenated in the stream of nitrogen and was irradiated for 0.25 h in UVA, under $N_2$, at 25° C., pH=6.5 while stirred. After 1 h of UVA exposition, the viscosity of the solution increased.

Method 7: Pmoc-DHA-HA (10 mg, 0.025 mmol, DS=10%, Mw=2.64×10⁵ g/mol) was dissolved in 3 mL of PBS (c=0.9%, pH=7.4) in a quartz flask. HA-aldehyde (20 mg, 0.050 mmol, DS=11%, Mw=5.10×10⁵ g/mol) was added. The sample was deoxygenated in the stream of nitrogen and was irradiated for 2 h in UVA, under $N_2$ at 25° C., pH=7.5 while stirred. After 2 h of UVA exposition, a gel was formed.

| | |
|---|---|
| DOSY NMR ($D_2O$) | log D (2.04 ppm, Ac—NH-polymer)~−11.5 m²/s |
| | log D (7.49 ppm, —N=CH—)~−11.5 m²/s |
| | log D (4.75 ppm, $H_2O$)~−8.6 m²/s |

Example 11. Photolysis of Pmoc-DHA-HA in the Presence of α,β-Unsaturated HA-Aldehyde and Crosslinking Method 1: Pmoc-DHA-HA (10 mg, 0.025 mmol, DS=10%, Mw=2.64×10⁵ g/mol) was dissolved in 2 mL of $D_2O$ in a quartz flask. α,β-Unsaturated HA-aldehyde (10 mg, 0.025 mmol, DS=5%, Mw=0.68×10⁵ g/mol) was added. The sample was deoxygenated in the stream of nitrogen and was irradiated for 1 h in UVA, under $N_2$, at 25° C., pH=7 while stirred, wherein samples for ¹H NMR analysis were taken in 15 minute intervals. After 60 min of UVA exposition, 75% of hydrazone (δ=7.58 ppm (H6) and 5.60 ppm (H4), HA-CH=N-HA) was formed.

Method 2: Pmoc-DHA-HA (10 mg, 0.025 mmol, DS=10%, Mw=2.64×10⁵ g/mol) was dissolved in 2 mL of PBS (0.9%, pH=7.4) in a quartz flask. α,β-unsaturated HA-aldehyde (10 mg, 0.025 mmol, DS=4%, Mw=2.05×10⁵ g/mol) was added. The sample was deoxygenated in the stream of nitrogen and was irradiated for 1 h in UVA, under $N_2$, at 25° C., pH=7 while stirred. After 1 h exposition, the viscosity of the solution increased.

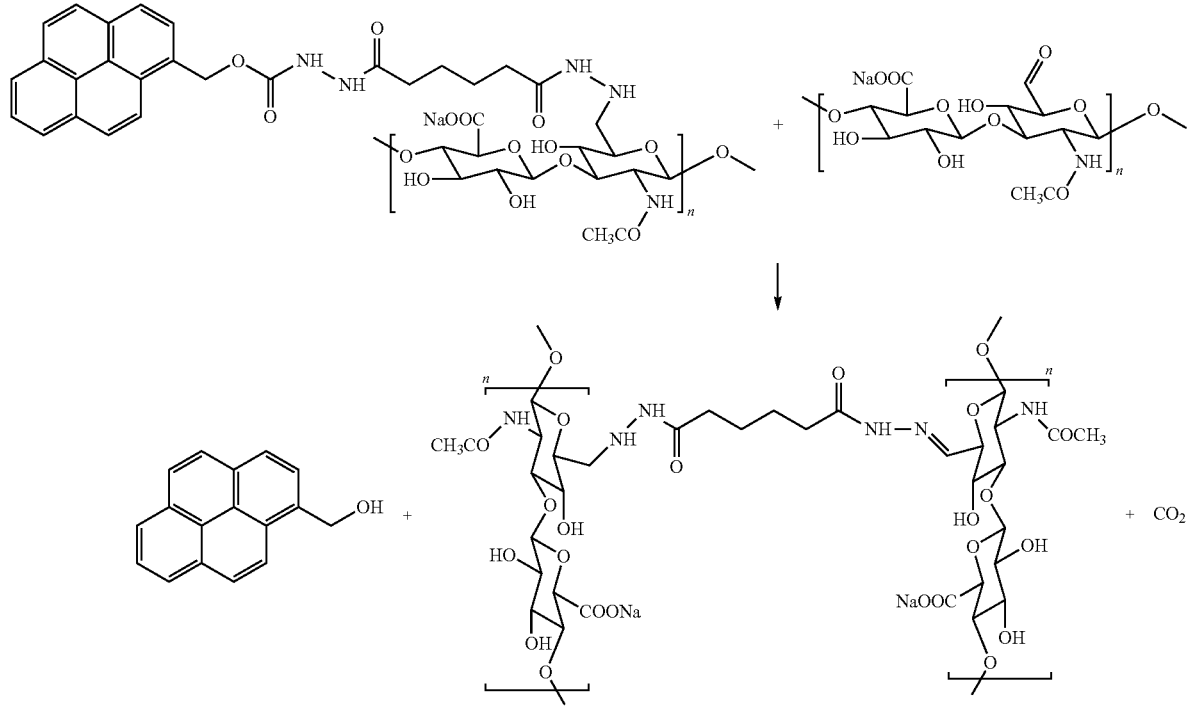

DS=3%, hydrazone group

| | |
|---|---|
| ¹H NMR ($D_2O$) | δ 7.49 (bs, 1H, —N=CH—) ppm |
| HSQC ($D_2O$) cross-peak | δ 7.49 (¹H)-146.6 (¹³C) ppm |

Method 3: Pmoc-DHA-HA (10 mg, 0.025 mmol, DS=10%, Mw=2.64×10⁵ g/mol) was dissolved in 3 mL of PBS (0.9%, pH=7.4) in a quartz flask. α,β-unsaturated HA-aldehyde (20 mg, 0.05 mmol, DS=4%, Mw=2.05×10⁵ g/mol) was added. The sample was deoxygenated in the stream of nitrogen and was irradiated for 1 h in UVA, under N₂, at 25° C., pH=7 while stirred. After 1 h of UVA, the viscosity of the solution increased.

Method 4: Pmoc-DHA-HA (20 mg, 0.05 mmol, DS=10%, Mw=2.64×10⁵ g/mol) was dissolved in 3 mL of PBS (0.9%, pH=7.4) in a quartz flask. α,β-unsaturated HA-aldehyde (10 mg, 0.025 mmol, DS=4%, Mw=2.05×10⁵ g/mol) was added. The sample was deoxygenated in the stream of nitrogen and was irradiated for 1 h in UVA, under N₂, at 25° C., pH=7 while stirred. After 1 h of UVA, the viscosity of the solution increased.

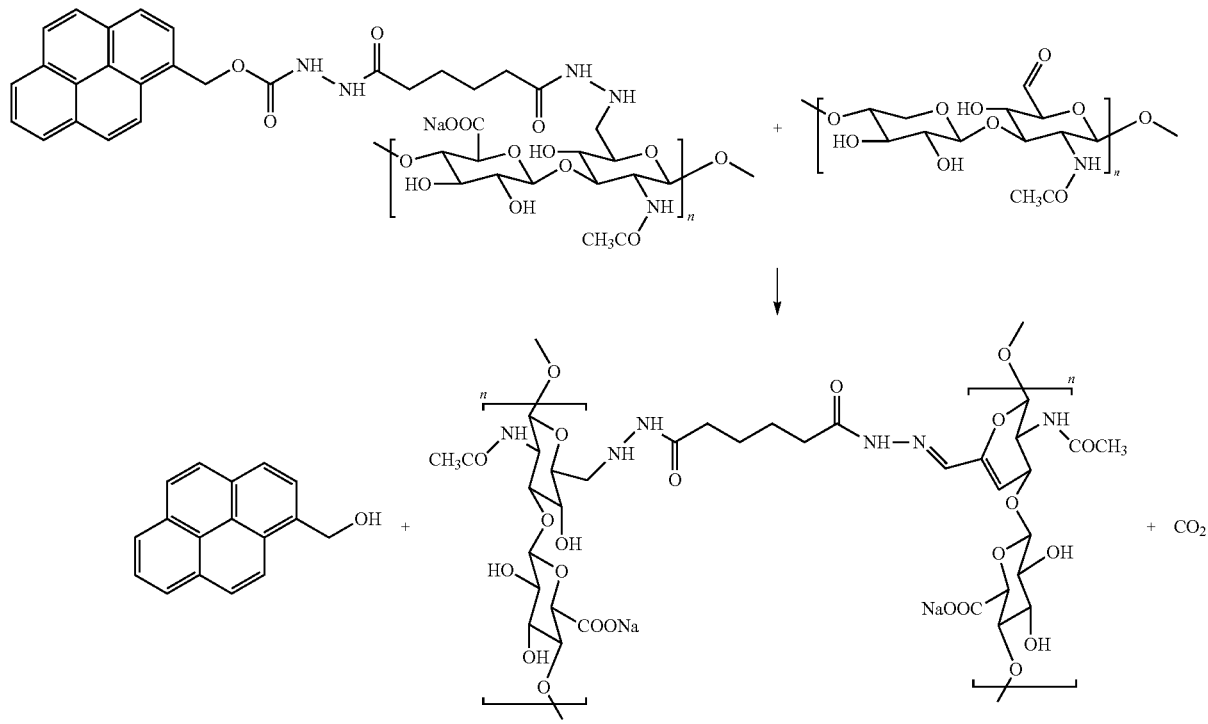

40

DS=3%, hydrazone

| ¹H NMR (D₂O) | δ 7.58 (bs, 1H, —N=CH—); |
| --- | --- |
| | 5.60 (bs, 1H, —CH=C—) ppm |
| HSQC (D₂O) cross-peak | δ 7.58 (¹H)-147.3 (¹³C); 5.60 (¹H)-110.30 (¹³C) ppm |
| DOSY NMR (D₂O) | log D (2.04 ppm, Ac—NH-polymer)~−11.2 m²/s |
| | log D (5.60 ppm, —CH=C—)~−11.2 m²/s |
| | log D (7.58 ppm, —N=CH—)~−11.2 m²/s |
| | log D (4.75 ppm, H₂O)~−8.6 m²/s |

Example 12. Photolysis of Pmoc-DHA-CS in the Presence of Saturated HA-Aldehyde and Crosslinking Method 1: Pmoc-DHA-CS (10 mg, 0.020 mmol, DS=5%, Mw=2-4×10⁴ g/mol) was dissolved in 1 mL of D₂O in a quartz flask. HA-aldehyde (8 mg, 0.020 mmol, DS=33%, Mw=0.40×10⁵ g/mol) was added. The sample was deoxygenated in the stream of nitrogen and was irradiated for 1 h in UVA, under N₂, at 25° C., pH=7 while stirred. After 60 min of UVA exposition, 100% of hydrazone (δ=7.60 ppm, HA-CH=N-DHA-CS) was formed.

Method 2: Pmoc-DHA-CS (10 mg, 0.020 mmol, DS=5%, Mw=2-4×10$^4$ g/mol) was dissolved in 1 mL of PBS (c=0.9%, pH=7.4) in a quartz flask. HA aldehyde (8 mg, 0.025 mmol, DS=33%, Mw=0.40×10$^5$ g/mol) was added. The sample was deoxygenated in the stream of nitrogen and was irradiated for 1 h in UVA, under N$_2$, at 25° C., pH=7 while stirred. After 1 h of UVA exposition, 70% of hydrazone was formed.

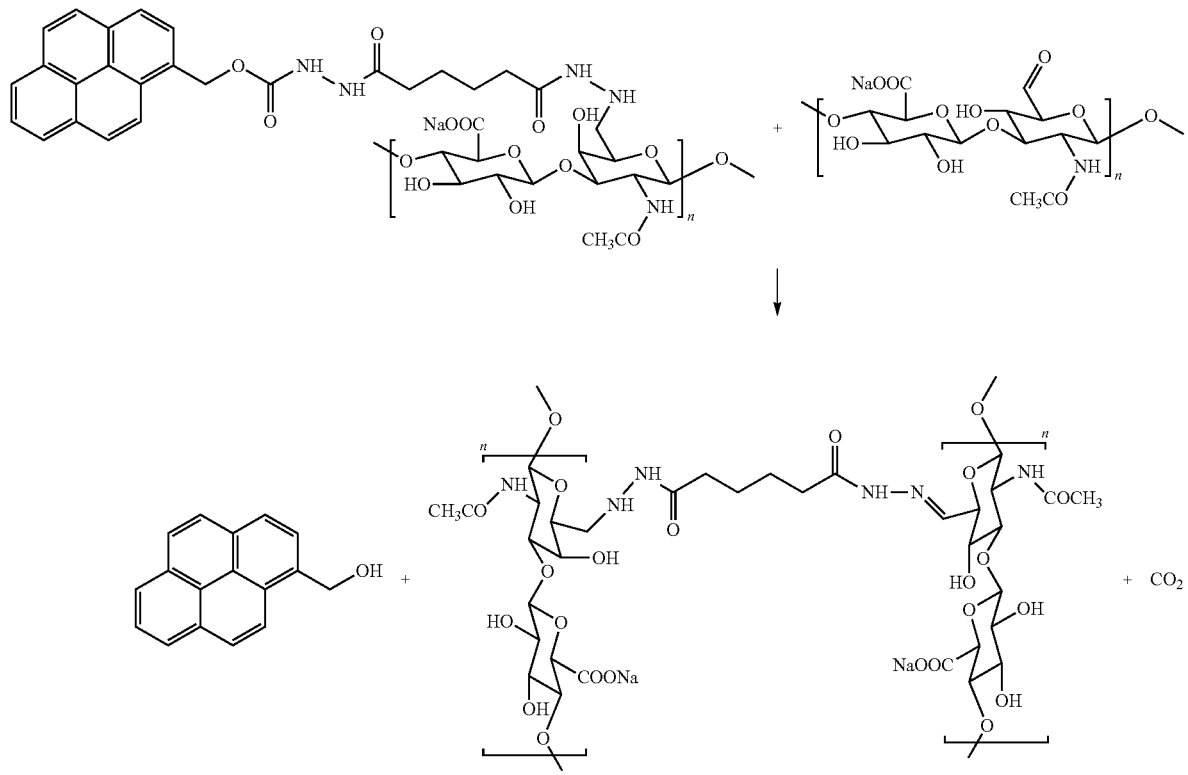

DS=5%, hydrazone group

| $^1$H NMR (D$_2$O) | δ 7.60 (bs, 1H, —N=CH—) ppm |
|---|---|
| HSQC (D$_2$O) cross-peak | δ 7.60 ($^1$H)-145.0 ($^{13}$C) ppm |
| DOSY NMR (D$_2$O) | log D (2.04 ppm, Ac—NH-polymer)~−11.2 m$^2$/s |
| | log D (7.60 ppm, —N=CH—)~−11.2 m$^2$/s |
| | log D (4.75 ppm, H$_2$O)~−8.6 m$^2$/s |

Example 13. Photolysis of Pmoc-DHA-CMCNa in the Presence of Saturated HA Aldehyde and Crosslinking Method 1: Pmoc-DHA-CMCNa (10 mg, 0.038 mmol, DS=3-4%, Mw=6-8×10$^4$ g/mol) was dissolved in 1 mL of D$_2$O in a quartz flask. HA-aldehyde (15 mg, 0.038 mmol, DS=33%, Mw=0.40×10$^5$ g/mol). The sample was deoxygenated in the stream of nitrogen and was irradiated for 1 h in UVA, under N$_2$, at 25° C., pH=7. After 60 min of UVA exposition, 100% of hydrazone (δ=7.55 and 7.60 ppm, HA-CH=N-DHA-CMC) was formed.

Method 2: Pmoc-DHA-CMCNa (10 mg, 0.038 mmol, DS=3-4%, Mw=6-8×10⁴ g/mol) was dissolved in 1 mL of PBS (c=0.9%, pH=7.4) in a quartz flask. HA-aldehyde (15 mg, 0.038 mmol, DS=33%, Mw=0.40×10³ g/mol) was added. The sample was deoxygenated in the stream of nitrogen and was irradiated for 1 h in UVA, under $N_2$, at 25° C., pH=7 while stirred. After 1 h of UVA exposition, 90% of hydrazone was formed.

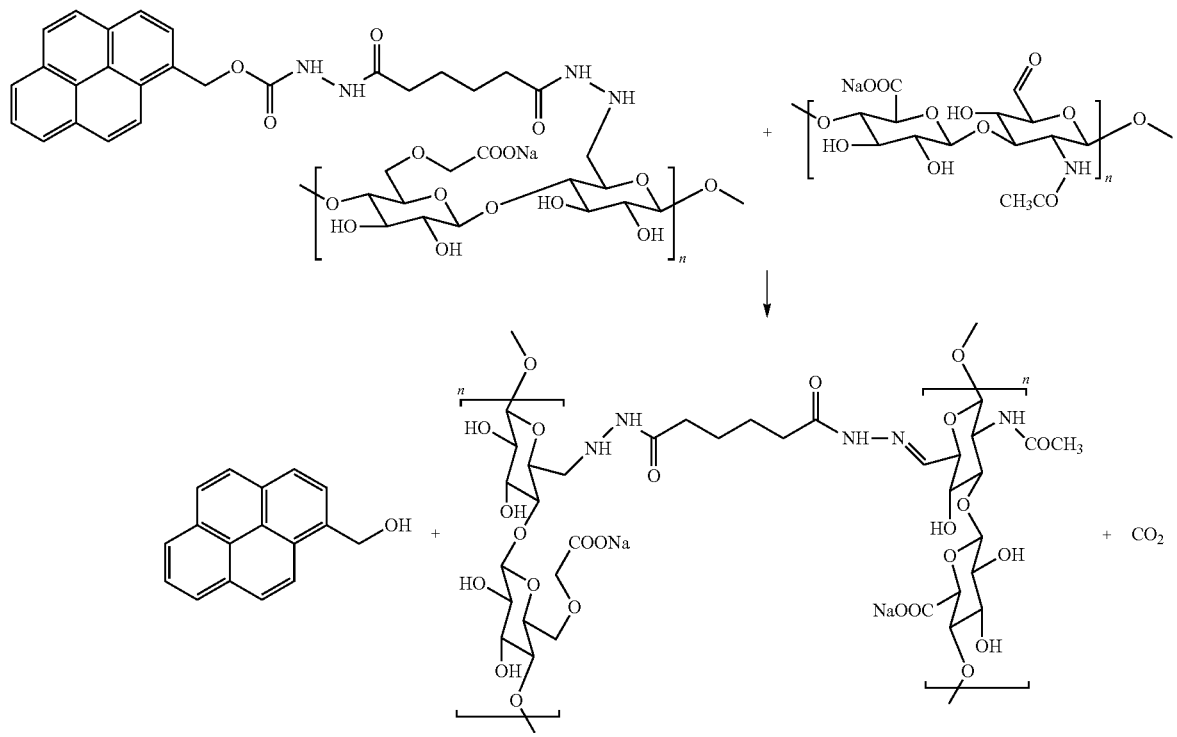

| DS=4%, hydrazone group | |
| --- | --- |
| ¹H NMR (D₂O) | δ 7.55 and 7.60 (bs, 1H, —N=CH—) ppm |
| HSQC (D₂O) cross-peak | δ 7.55 (¹H)-148.2 (¹³C); 7.60 (¹H)-148.2 (¹³C); ppm |
| DOSY NMR (D₂O) | log D (2.04 ppm, Ac—NH-HA)~−11.4 m²/s |
| | log D (4.55-4.60 ppm, H1aH1'-CMCNa)~−11.4 m²/s |
| | log D (7.55 and 7.60 ppm, —N=CH—)~−11.4 m²/s |
| | log D (4.75 ppm, H₂O)~−8.6 m²/s |

Example 14 Photolysis of Pmoc-DHA-CS in the Presence of Saturated CS-Aldehyde and Crosslinking Pmoc-DHA-CS (10 mg, 0.020 mmol, DS=5%, Mw=2-4×10⁴ g/mol) was dissolved in 1 mL of PBS (c=0.9%, pH=7.4) in a quartz flask. CS (10 mg, 0.02 mmol, DS=5%) was added. The sample was deoxygenated in the stream of nitrogen and was irradiated for 1 h in UVA, under $N_2$ at 25° C., pH=7, while stirred. After 60 min of UVA exposition, the viscosity increased.

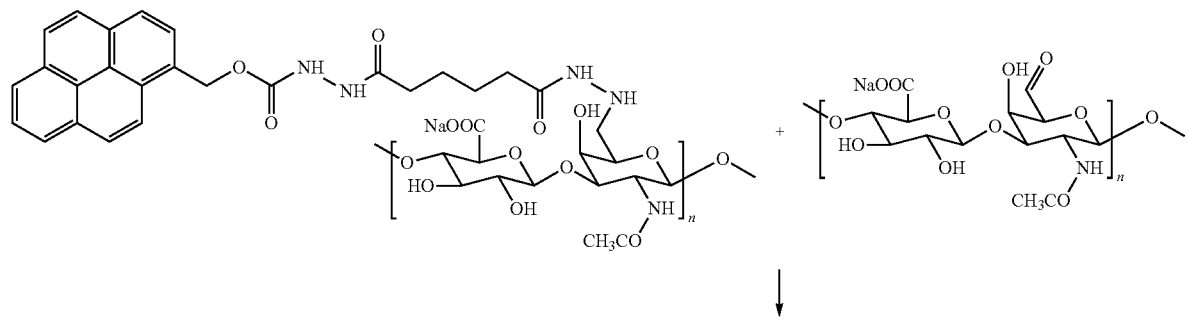

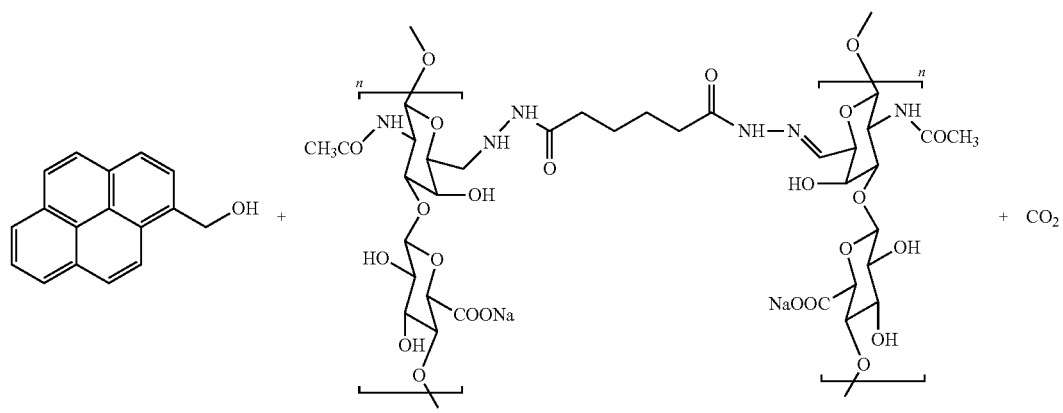

$^1$H NMR (D$_2$O) δ 7.55-7.60 (bs, 1H, —N=CH—) ppm

Example 15. Photolysis of Pmoc-DHA-CMCNa in the Presence of CMCNa-Aldehyde and Crosslinking Pmoc-DHA-CMCNa (10 mg, 0.038 mmol, DS=3-4%, Mw=0.60-0.80×10$^5$ g/mol) was dissolved in 1 mL of PBS (c=0.9%, pH=7.4) in a quartz flask. CMCNa-aldehyde (9 mg, 0.038 mmol, DS=3-4%, Mw=0.6×10$^5$ g/mol) was added. The sample was deoxygenated in the stream of nitrogen and was irradiated for 1 h in UVA, under N$_2$, at 25° C., pH=7 while stirred. After 60 min of UVA exposition, the viscosity increased.

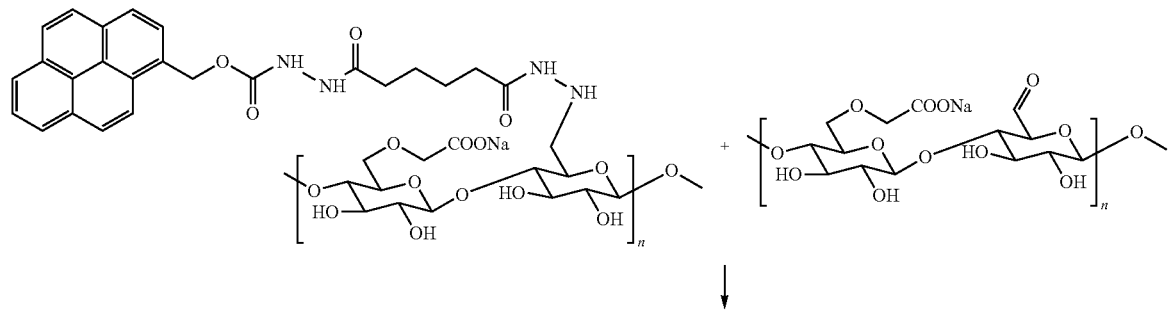

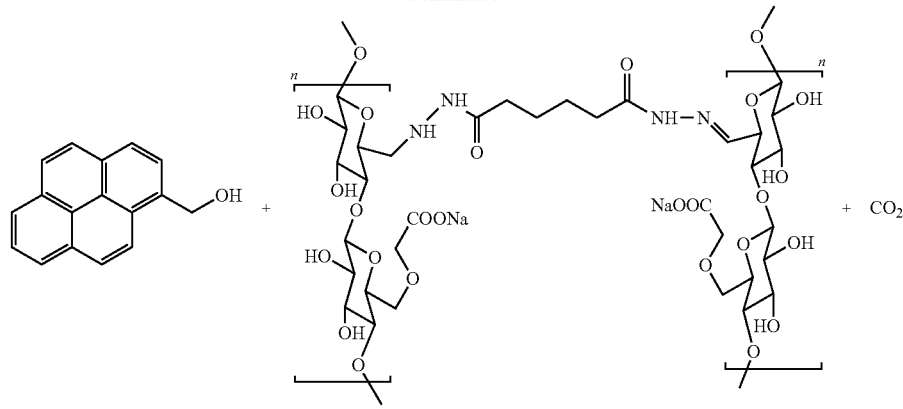

$^1$H NMR (D$_2$O) δ 7.55-7.60 (bs, 1H, —N═CH—) ppm

The invention claimed is:

1. A method of preparation of crosslinked polysaccharide materials according to the general formula (I)

polysaccharide1-R$^1$—N═CH-polysaccharide2 (I)

where polysaccharide1 and polysaccharide2 are identical or different polysaccharides and R$^1$ is C$_1$-C$_{30}$ alkyl residue, C$_1$-C$_{30}$ alkylaryl residue or C$_1$-C$_{30}$ alkylheteroaryl residue, optionally containing one or more identical or different heteroatoms selected from the group comprising N, O, S, characterized in that an aqueous solution of aldehyde of polysaccharide 2 according to the general formula III polysaccharide2-CH═O (III), where the substitution degree of aldehyde in polysaccharide2 is within the range of 1 to 50%, is added to an aqueous solution of polysaccharide 1 substituted on the site of amino group by a photoremovable group, according to the general formula II polysaccharide1-R$^1$—NH—CO—O—CH$_2$—R$^2$ (II), where R$^1$ is defined above; R$^2$ is an aromatic system, and where the substitution degree of carbamate in polysaccharide 1 is within the range of 1 to 10%, and the formed mixture is subjected to electromagnetic radiation and deoxygenation simultaneously.

2. The method of preparation according to claim 1, characterized in that the substitution degree of carbamate in polysaccharide 1 is within the range of 3 to 10% and its molecular weight is 10 to 400 kDa.

3. The method of preparation according to claim 1, characterized in that the substitution degree of aldehyde in polysaccharide 2 is within the range of 3 to 25% and its molecular mass is 10 to 800 kDa.

4. The method of preparation according to claim 1, characterized in that polysaccharide 1 and polysaccharide 2 are selected from the group comprising hyaluronan, chondroitin sulfate, cellulose and pharmaceutically acceptable derivatives and/or salts thereof.

5. The method of preparation according to claim 1, characterized in that R$^1$ is selected from the group comprising adipic acid dihydrazide and hexamethylene diamine.

6. The method of preparation according to claim 1, characterized in that R$^2$ is selected from the group comprising pyrene, anthracene, phenanthrene, perylene, anthraquinone, coumarin and substitution derivatives thereof, that can contain atoms C, H, O, S, N in their structure and that exhibit absorption of electromagnetic radiation.

7. The method of preparation according to claim 1, characterized in that the weight ratio of polysaccharide 1 to polysaccharide 2 is within the range of 1:2 to 2:1.

8. The method of preparation according to claim 1, characterized in that the mixture is subjected to electromagnetic radiation for 0.25 to 2 hours at the temperature of 10 to 50° C.

9. The method of preparation according to claim 1, characterized in that the aqueous solutions of polysaccharides 1 and 2 further contain water soluble agents selected from the group comprising inorganic salts or buffers wherein pH of the solution is within the range of 6.5 to 7.5.

10. The method of preparation according to claim 1, characterized in that electromagnetic radiation of wavelength 320-400 nm is used.

11. The method of preparation according to claim 1, characterized in that the reaction is temporal controlled by means of a switch of the electromagnetic radiation source or by means of a pulse source of electromagnetic radiation or by means of shading of the reaction.

12. The method of preparation according to claim 1, characterized in that the reaction is spatially controlled by means of a photomask, focused electromagnetic radiation or a beam of electromagnetic radiation.

* * * * *

UNITED STATES PATENT AND TRADEMARK OFFICE
CERTIFICATE OF CORRECTION

PATENT NO.         : 10,759,878 B2
APPLICATION NO.    : 15/736113
DATED              : September 1, 2020
INVENTOR(S)        : Tomas Bobula et al.

It is certified that error appears in the above-identified patent and that said Letters Patent is hereby corrected as shown below:

In the Specification

Column 3, Line 18, "pbotomask" should be --photomask--.

Column 3, Line 47, "ammines," should be --amines,--.

Column 22, upper right quandrant of equation, " 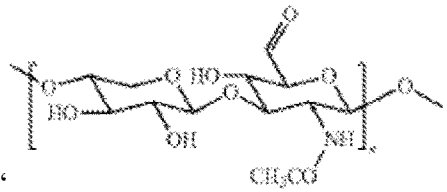 " should be 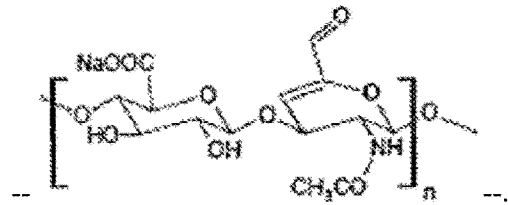 --.

Signed and Sealed this
Third Day of November, 2020

Andrei Iancu
*Director of the United States Patent and Trademark Office*